US011844356B2

(12) United States Patent
Soe et al.

(10) Patent No.: US 11,844,356 B2
(45) Date of Patent: Dec. 19, 2023

(54) ENZYMATIC MODIFICATION OF WHEAT PHOSPHOLIPIDS IN BAKERY APPLICATIONS

(71) Applicant: DUPONT NUTRITION BIOSCIENCES APS, Copenhagen (DK)

(72) Inventors: Jorn Borch Soe, Tilst (DK); Rene Mikkelsen, Hovedgaard (DK); Tina Lillan Joergensen, Silkeborg (DK)

(73) Assignee: DuPont Nutrition Biosciences APS, Kongens Lyngby (DK)

( * ) Notice: Subject to any disclaimer, the term of this patent is extended or adjusted under 35 U.S.C. 154(b) by 65 days.

(21) Appl. No.: 17/242,982

(22) Filed: Apr. 28, 2021

(65) Prior Publication Data

US 2021/0251244 A1  Aug. 19, 2021

Related U.S. Application Data

(63) Continuation of application No. 16/064,218, filed as application No. PCT/US2016/067942 on Dec. 21, 2016, now abandoned.

(Continued)

(30) Foreign Application Priority Data

Dec. 22, 2015 (GB) ..................... 1522681

(51) Int. Cl.
*A21D 2/16* (2006.01)
*A21D 8/04* (2006.01)
(Continued)

(52) U.S. Cl.
CPC .............. *A21D 2/165* (2013.01); *A21D 8/042* (2013.01); *C11B 3/003* (2013.01); *C11C 3/00* (2013.01);
(Continued)

(58) Field of Classification Search
CPC ... C12N 9/20; C12N 9/16; C12N 9/18; C12Y 301/01026; C12Y 301/01004;
(Continued)

(56) References Cited

U.S. PATENT DOCUMENTS 8,309,147 B2 * 11/2012 Jorgensen ................ C12N 9/18
426/52

FOREIGN PATENT DOCUMENTS

CN   104432106 A   3/2015
JP   2003213288 A   7/2003
(Continued)

OTHER PUBLICATIONS

Arunga et al., "The Structural Analysis of Wheat Flour Glycerolipids", Lipids, vol. 6, No. 10, 1971, p. 768-776.
(Continued)

*Primary Examiner* — Subbalakshmi Prakash

(57) ABSTRACT

The present invention relates to a method of making a dough, said method comprises admixing a dough component, a phospholipase A2 enzyme which acts on N-acyl phosphatidyl ethanolamine at the sn2 position, and an enzyme that acts on a polar lipid at the sn1 position. A food enzyme composition comprising: a phospholipase A2 enzyme which is capable of acting on N-acylphosphatidyl ethanolamine at the sn2 position; and an enzyme that acts on a polar lipid at the sn1 position is also taught.

9 Claims, 7 Drawing Sheets

Specification includes a Sequence Listing.

Related U.S. Application Data

(60) Provisional application No. 62/319,399, filed on Apr. 7, 2016.

(51) Int. Cl.
    *C11C 3/08*        (2006.01)
    *C12N 9/20*        (2006.01)
    *C12N 9/16*        (2006.01)
    *C12N 9/18*        (2006.01)
    *C11C 3/00*        (2006.01)
    *C11B 3/00*        (2006.01)

(52) U.S. Cl.
    CPC .................. *C11C 3/08* (2013.01); *C12N 9/16* (2013.01); *C12N 9/18* (2013.01); *C12N 9/20* (2013.01); *C12Y 301/01004* (2013.01); *C12Y 301/01026* (2013.01); *C12Y 301/01032* (2013.01)

(58) Field of Classification Search
    CPC ..... C12Y 301/01032; C11C 3/08; C11C 3/00; C11B 3/003; A21D 8/042; A21D 2/165
    USPC .......................................................... 426/20
    See application file for complete search history.

(56) References Cited

FOREIGN PATENT DOCUMENTS

| WO | 0203805 A1 | 1/2002 |
|---|---|---|
| WO | 03070013 A1 | 8/2003 |
| WO | 2005001036 A1 | 1/2005 |
| WO | 2010081869 A1 | 7/2010 |

OTHER PUBLICATIONS

Gaffney et al., "Synthesis of naturally occurring phosphatidylinositol 3,4,5-trisphosphate [PtdIns(3,4,5)P3] and its diastereoisomers", Journal of the Chemical Society, Perkin Transactions 1, Issue 2, 2001, pp. 192-205.

Gerits et al., "Native and enzymatically modified wheat (*Triticum aestivum* L.) endogenous lipids in bread making: A focus on gas cell stabilization mechanisms", Food Chemistry, vol. 172, 2015, pp. 613-621.

Petersen et al., "SignalP 4.0: discriminating signal peptides from transmembrane regions", Nature Methods, vol. 8, 2011, pp. 785-786.

Schaffarczyk et al., "Lipases in Wheat Breadmaking: Analysis and Functional Effects of Lipid Reaction Products", J. Agric. Food Chem. 62(32), 2014, pp. 8229-8237.

Selmair et al., "Baking Performance of Synthetic Glycolipids in Comparison to Commercial Surfactants", Journal of Agricultural and Food Chemistry, vol. 56(15), Aug. 2008, pp. 6691-6700.

Te'o et al., "Biolistic transformation of Trichoderma reesei using the Bio-Rad seven barrels Hepta Adaptor system", J Microbiol Methods, vol. 51(3), 2002, pp. 393-399.

International Search Report and Written Opinion from PCT App. No. PCT/US2016/067942 dated Mar. 16, 2017, 13 pages.

* cited by examiner

Composition of total wheat flour lipids

FIGURE 4

(SEQ ID NO: 1)

| | |
|---|---|
| 1 | EAEAAVGVTS TDFTNFKFYI QHGAAAYCNS GTAAGAKITC SNNGCPTIES |
| 51 | NGVTVVASFT GSKTGIGGYV STDSSRKEIV VAIRGSSNIR NWLTNLDFDQ |
| 101 | SDCSLVSGCG VHSGFQNAWA EISAQASAAV AKARKANPSF KVVATGHSLG |
| 151 | GAVATLSAAN LRAAGTPVDI YTYGAPRVGN AALSAFISNQ AGGEFRVTHD |
| 201 | KDPVPRLPPL IFGYRHTTPE YWLSGGGGDK VDYAISDVKV CEGAANLMCN |
| 251 | GGTLGLDIDA HLHYFQATDA CNAGGFSWR |

FIGURE 5

(SEQ ID NO: 4)

LPSIGKADAALVPRQSAIQITDQYLFDLTLPAFTAKRNARDPPSLIWDSDGCSSSPDNPFGF
PFVPACHRHDFGYRNYKAQNRFTDAGKLSIDNNFKSDLYYQCESVSAKTACRALADVYYA
AVRAFGGSTQDKRDDDLVKIYEEKVAIYNKAVEEAQAKGELWTLD

FIGURE 6

(SEQ ID NO: 5)

ATGAAGTTCCTGAGCACCGCACTTTGCCTTGCATCTTCTGTCCTGGCACTTCCATCTAT
CGGTAAAGCAGACGCAGCACTTGTTCCACGTCAATCTGCAATCCAGATCACCGACCAG
TACCTTTTCGACCTTACCCTTCCAGCATTCACCGCAAAACGTAACGCACGGGATCCACC
ATCTCTTATCTGGGATTCTGACGGCTGTAGCTCTTCTCCAGATAACCCATTCGGCTTCC
CATTCGTTCCTGCTTGTCATCGGCATGATTTCGGTTACCGGAACTACAAGGCACAGAAC
CGTTTCACCGACGCAGGCAAGCTTTCTATTGACAACAACTTCAAGAGCGACCTCTACTA
CCAGTGCGAGTCTGTTTCTGCAAAGACAGCTTGTCGGGCACTTGCAGACGTCTATTAC
GCAGCAGTTCGGGCATTCGGAGGTTCTACACAAGATAAGCGGGACGACGATCTAGTTA
AGATCTACGAAGAGAAGGTCGCCATCTACAACAAGGCAGTTGAAGAGGCACAAGCAAA
GGGCGAGCTTTGGACACTTGAT

ENZYMATIC MODIFICATION OF WHEAT PHOSPHOLIPIDS IN BAKERY APPLICATIONS

CROSS-REFERENCE TO RELATED APPLICATIONS

This application is a continuation application of U.S. patent application Ser. No. 16/064,218 (filed Jun. 20, 2018; and published on Dec. 27, 2018 as Publication No. US 2018-0368424 A1), which claims priority under 35 USC § 371 as a national phase of International Patent Application No. PCT/US2016/067942 (filed Dec. 21, 2016; and published on Jun. 29, 2017 as Publication No. WO2017112734 A1), which claims priority to and the benefit of U.S. Provisional Application Ser. No. 62/319,399, filed Apr. 7, 2016 and United Kingdom Patent Application No. GB 1522681.4, filed Dec. 22, 2015, all of which are hereby incorporated by reference in their entirety.

TECHNICAL FIELD

The present invention relates to novel enzyme combinations and their use in the manufacture of dough or baked products. The present invention further relates to methods of making dough or a baked product using novel enzyme combinations.

BACKGROUND

Lipids constitute approximately 2% of wheat flour and these lipids are considered highly important for the baking quality of wheat flour. Wheat flour lipids can be divided into non-polar and polar lipids, and it has been shown that improved baking and bread properties are mainly due to polar lipids.

Over the past few decades, an increased demand for consistent and higher quality baked goods has led to the application of a wide range of additives. In the baking industry it is known to supplement endogenous lipids with natural polar lipids, like lecithin, or additional enzymes, such as lipases.

One of the most abundant phospholipids in wheat flour is N-acyl phosphatidyl ethanolamine (NAPE), which by enzymatic hydrolysis is converted to N-acyl lysophosphatidyl ethanolamine (NALPE). Further hydrolysis of NALPE produces N-acyl glycerophospho-ethanolamine (NAGPE).

SUMMARY OF THE INVENTION

Accordingly, the first aspect of the present invention provides a food enzyme composition comprising: a phospholipase A2 enzyme which acts on N-acyl phosphatidyl ethanolamine at the sn2 position; and an enzyme that acts on a polar lipid at the sn1 position.

In a further aspect, there is provided a method of making a dough, said method comprising admixing a dough component, a phospholipase A2 enzyme which acts on N-acyl phosphatidyl ethanolamine at the sn2 position, and an enzyme that acts on a polar lipid at the sn1 position.

In a yet further aspect the invention provides the use of a phospholipase A2 enzyme which acts on N-acyl phosphatidyl ethanolamine at the sn2 position and an enzyme that acts on a polar lipid at the sn1 position in the manufacture of a dough or a baked product for improving the specific volume of a baked product; dough characteristics (such as dough development; dough extensibility); improving crust crispiness of a baked product; improving the crumb structure (such as improving crumb pore size of a baked product or improving crumb pore homogeneity of a baked product); improving softness (such as improving softness of a baked product); improving the oven spring of a baked product; increasing N-acyl lysophosphatidyl ethanolamine in the dough and/or baked product (preferably increasing N-acyl lysophosphatidyl ethanolamine having a fatty acid moiety containing 14-20 carbon atoms, preferably increasing N-acyl lysophosphatidyl ethanolamine having a saturated fatty acid moiety containing 14-20 carbon atoms); increasing a lyso-phospholipid in the dough and/or baked product; increasing a digalactosylmonoglyceride and/or monogalactosylmonoglyceride in the dough and/or baked product; increasing N-acyl lysophosphatidyl ethanolamine together with increasing a lyso-phospholipid and/or a digalactosylmonoglyceride and/or monogalactosylmonoglyceride in the dough and/or baked product.

In a yet further aspect there is provided a kit comprising a phospholipase A2 enzyme which is capable of acting on N-acylphosphatidyl ethanolamine at the sn2 position; an enzyme that acts on a polar lipid at the sn1 position; and a set of instructions for use.

The present invention yet further provides a dough obtainable by (preferably obtained by) a method according to the present invention or a baked product obtainable by (preferably obtained by) a method according to the present invention.

BRIEF DESCRIPTION OF THE BIOLOGICAL SEQUENCES

The following sequences comply with 37 C.F.R. §§ 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the European Patent Convention (EPC) and the Patent Cooperation Treaty (PCT) Rules 5.2 and 49.5(a-bis), and Section 208 and Annex C of the Administrative Instructions. The symbols and format used for nucleotide and amino acid sequence data comply with the rules set forth in 37 C.F.R. § 1.822.

SEQ ID NO: 1 is the amino acid sequence of an enzyme in POWERBAKE® 4080 and POWERBAKE®4090 that acts on a polar lipid at the sn1 position (same as SEQ ID NO: 6 from U.S. Pat. No. 8,012,732; hereby incorporated by reference). This enzyme is known to have both galactolipase and phospholipase activity.

SEQ ID NO: 2 is the amino acid sequence of a mature lipid acyltransferase (GCAT) derived from *Aeromonas salmonicida* (See U.S. Pat. No. 9,175,271).

SEQ ID NO: 3 is the amino acid sequence of a phospholipase A2 enzyme which acts on N-acyl phosphatidyl ethanolamine at the sn2 position found in MAXAPAL® A2.

SEQ ID NO: 4 is the amino acid sequence of a phospholipase A2 enzyme (CRC08335) which acts on NAPE (N-acyl phosphatidyl ethanolamine) at the sn2 position.

SEQ ID NO: 5 is the nucleotide sequence of a phospholipase A2 enzyme (CRC08335) which acts on NAPE (N-acyl phosphatidyl ethanolamine) at the sn2 position.

SEQ ID NO: 6 is an N-terminal predicted signal peptide sequence of CRC08335.

DESCRIPTION OF FIGURES

FIG. 4 shows the amino acid sequence (SEQ ID NO: 1) of POWERBAKE®4080 and POWERBAKE®4090 (both commercially available from DuPont Nutrition Biosciences ApS).

FIG. 5 shows the amino acid sequence (SEQ ID NO: 4) of CRC08335.

FIG. 6 shows the nucleotide sequence (SEQ ID NO: 5) of CRC08335.

ABBREVIATIONS

Figure 1:
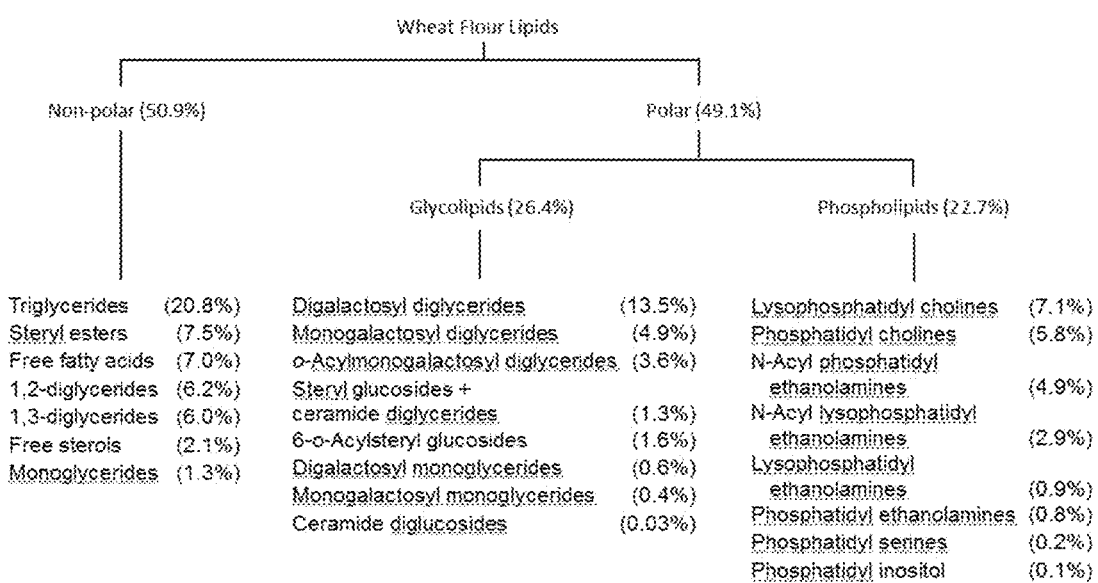
FIG. 1 shows a list of polar and non-polar lipids found in flour (particularly wheat flour) from Pomeranz, Y. in Modern Cereal Science and Technology ((1987) VCH Publishers, New York, NY).

NAPE—N-acyl phosphatidyl ethanolamine
NALPE—N-acyl lysophosphatidylethanolamine
NAGPE—N-acyl glycerophosphoethanolamine
DGDG—digalactosyldiglyceride
DGMG—digalactosylmonoglyceride
MGDG—monogalactosyldiglyceride
MGMG—monogalactosylmonoglyceride
PC—phosphatidylcholine
PLA—phospholipase A

DETAILED DESCRIPTION

A seminal finding of the present invention is that advantageous properties in a foodstuff (e.g. a dough and/or a baked product) can be achieved by using a combination of a phospholipase A2 enzyme which acts on N-acyl phosphatidyl ethanolamine (NAPE) at the sn2 position and an enzyme that acts on a polar lipid at the sn1 position.

For the first time the present inventors have shown the synergistic effects provided by the combination of a phospholipase A2 enzyme which is capable of acting on NAPE at the sn2 position and an enzyme that acts on a polar lipid at the sn1 position in a foodstuff, e.g. a dough or a baked product.

Based on these findings, there are provided methods and uses of a phospholipase A2 enzyme which is capable of acting on NAPE at the sn2 position; and an enzyme that acts on a polar lipid at the sn1 position in the preparation of a dough or products obtainable from the dough. The present invention yet further provides a food enzyme composition comprising a phospholipase A2 enzyme which is capable of acting on NAPE at the sn2 position; and an enzyme that acts on a polar lipid at the sn1 position.

The present invention relates to the lysis of specific polar lipids in a specific way in dough and food products obtainable from the dough.

The polar lipids contained in most cereal flours include phospholipids and galactolipids.

A significant amount of phospholipids in flour, particularly wheat flour, may be N-acyl phosphatidyl ethanolamine (NAPE). Schafferczyk et al (J. of Agricultural and Food Chemistry (2014) 62: 8229-8237) teaches that wheat flour contains on average 0.1% NAPE compared with 0.02% phosphatidylcholine (PC).

Flour, particularly wheat flour, may comprise galactolipids. Galactolipids such as digalactosyldiglyceride (DGDG) or monogalactosyldiglyceride (MGDG) are naturally occurring (or endogenous) lipid components in flour, particularly wheat flour.

Preferably the phospholipids and/or galactolipids acted on by the enzymes used in the present invention are naturally occurring phospholipids and/or galactolipids within the flour.

The phospholipase A2 enzyme which acts on NAPE at the sn2 position according to the present invention is one which has PLA2 activity in the "Assay for the Determination of phospholipase activity and position specificity on NAPE" taught herein.

Assay for the Determination of phospholipase activity and position specificity on NAPE:

Substrate: 0.6% 16:0-18:1 NAPE(N-linoleoyl-(1-palmitoyl-2-oleoyl-sn-glycero-3-phosphoethanolamine) (obtained from Avanti on request or produced according to J. L. Newman et al., Chemistry and Physics of Lipids (1986) 42: 240-260), 0.4% TRITON™-X 100 (Sigma Aldrich, St. Louis, MO; X-100), and 5 mM $CaCl_2$) were dissolved in 0.05M HEPES buffer pH 7.0. For pancreatic enzyme 0,003 M Deoxycholate was also added.

Assay Procedure:

2 mL substrate was incubated at 30° C. and added 0.1 mL enzyme solution (approx. 5 TIPU/mL or an enzyme amount corresponding to 2-5% substrate consumed after 10 minutes reaction) in 0.05 M HEPES buffer and incubated with magnetic stirring for 10 minutes at 30° C. 40 µL 4 M HCl is added to stop the reaction and to protonate the free fatty acids. 1 mL 99% ethanol is added and mixed on a Vortex mixer. 5 mL MTBE (methyl tert-butyl ether) containing 0.5 mg C17:0 fatty acid (margaric acid) was added. The sample was mixed again on a Vortex mixer for 5 sec. and extracted for 30 min on a Rotamix at 25 rpm. The sample was centrifuged at 1520 g for 10 min.

One 500 mg amine ($NH_2$)—Bond Elut SPE column (Agilent Technologies, Santa Clara, CA) is placed on a Bond Elut Vacuum System. The column is conditioned with 8 mL Petroleum-ether. The MTBE phase from the extraction is applied onto the column and eluted with:

1. fraction 8 mL Solvent A: MTBE: 2-propanol, 2:1
2. fraction 8 mL Solvent B: Acetone: Formic acid 100:2

The solvents were eluted with approx. 0.25 mL/min.

The collected fatty acid fraction (fraction 2) is evaporated to dryness and fatty acid content is analyzed by GLC.

Based on the internal standard C17:0 fatty acid the amount of C16:0 and C18:1 fatty acid is determined.

Enzyme activity on NAPE is calculated as µmol fatty acid produced per minutes under assay conditions $$\text{Enzyme activity} = 2 \times A \times 1000000 \times D$$

i. $100 \times MV \times 10 \times 0.1$

Where

A=% C16:0 fatty acid+% C18:1 fatty acids
2=mL substrate
1000000=mol conversion to µmol D=Enzyme dilution factor
MV=average molecular weight of C16:0 and C18:1 fatty acids produced
10=minutes reaction time
b.=mL enzyme added to assay The enzyme specificity is calculated as:
Relative PLA1 activity=% C16:0×100
1. % C16:0+% C18:1
Relative PLA2 activity=% C18:1×100
2. % C16:0+% C18:1

A phospholipase A2 enzyme which preferentially lyses, e.g. hydrolyses, NAPE at the sn2 position would be one which in the "Assay for the Determination of phospholipase activity and position specificity on NAPE" taught herein has at least 50% more relative PLA2 activity on NAPE. An enzyme with 50% more relative PLA2 activity means that the enzyme has less than 25% sn1 activity and more than 75% sn2 activity. Preferably phospholipase A2 enzyme which preferentially lyses, e.g. hydrolyses, NAPE at the sn2 position would be one which in the "Assay for the Determination of phospholipase activity and position specificity on NAPE" taught herein has at least 10% more relative PLA2 activity compared with relative PLA1 activity.

Preferably to determine that the phospholipase A2 enzyme preferentially lyses, e.g. hydrolyses, NAPE at the sn2 position, the "Assay for the Determination of phospholipase activity and position specificity on NAPE" taught herein is used. However, in some embodiments this may be determined using the EnzChek Phospholipase A2 Assay Kit from Invitrogen cat. No. E10217, optionally together with a dough test which analyses whether the enzyme reduces NAPE with increased formation of NALPE in a dough.

The term "specifically" in relation to the phospholipase A2 enzyme which acts on NAPE at the sn2 position means that the enzyme will catalyse only one particular reaction, e.g. the lysis (or hydrolysis) of NAPE at the sn2 position to produce 1-NALPE. A phospholipase A2 enzyme which specifically lyses, e.g. hydrolyses, NAPE at the sn2 position would be one which in the "Assay for the Determination of phospholipase activity and position specificity on NAPE" taught herein has at least 80% more relative PLA2 activity than PLA1 activity. In one embodiment the phospholipase A2 enzyme which acts on NAPE at the sn2 position according to the present invention has one or more of the following enzyme activities: phospholipase A2 activity (e.g. E.C. 3.1.1.4) or lipid acyltransferase activity (e.g. E.C. 2.3.1.43).

According to another embodiment the phospholipase A2 enzyme which acts on NAPE at the sn2 position according to the present invention is one which is capable of converting NAPE into 1-NALPE under dough conditions.

According to another embodiment the phospholipase A2 enzyme which acts on NAPE at the sn2 position according to the present invention is one which converts NAPE into 1-NALPE wherein the fatty acid moiety of the produced NALPE contains 14-20 carbon atoms.

In one embodiment the phospholipase A2 enzyme which acts on NAPE at the sn2 position according to the present invention is one which converts NAPE into 1-NALPE wherein the fatty acid moiety of the produced NALPE is saturated and contains 14-20 carbon atoms.

In a further embodiment the phospholipase A2 enzyme which acts on NAPE at the sn2 position according to the present invention is one which converts NAPE into 1-NALPE wherein the fatty acid moiety of the produced NALPE is saturated and contains 16 carbon atoms (C16:0). A phospholipase A2 enzyme which converts NAPE into 1-NALPE wherein the fatty acid moiety of the produced NALPE is saturated and contains 16 carbon atoms can be determined using the "Assay for the Determination of phospholipase activity and position specificity on NAPE" taught herein and/or using "HPLC/MS method for analysis of phospholipids extracted from dough" taught herein.

In one embodiment use of the enzyme combination in accordance with the present invention results in the amount of C16:0 NALPE in the dough being increased by a factor of at least 1.5 compared with a dough without enzyme addition. For example the amount of C16:0 NALPE In the dough may be increased by a factor of at least 2.0, preferably at least 3.0.

In one embodiment use of the enzyme combination in accordance with the present invention results in the amount of C16:0 NALPE in the dough being increased by a factor of between about 1.5 and about 4.0 compared with a dough without enzyme addition.

Dough conditions are well known to one skilled in the art. These may include the conditions during the mixing of dough components or resting and storage of dough. Suitably dough conditions include dough mixing, dough resting, dough scaling and moulding, and dough fermentation.

According to another aspect of the present invention the claimed phospholipase A2 enzyme which acts on NAPE at the sn2 position is incapable or substantially incapable of acting on N-acyl lysophosphatidylethanolamine (NALPE).

The term "substantially incapable of acting on N-acyl lysophosphatidylethanolamine" as used herein means that the enzyme which in the same dosage tested in both the "Assay for the Determination of phospholipase activity and position specificity on NAPE" and in the "Assay for the Determination Lysophospholipase activity on N-acyl lysophosphatidylethanolamine (NALPE)" has less than 20% activity on NALPE compared to activity on NAPE. More preferably an enzyme which is substantially incapable of acting on N-acyl lysophosphatidylethanolamine has less than 10% activity on NALPE compared with activity on NAPE, more suitably less than 5% activity on NALPE, even more preferably less than 1% NALPE activity. The determination of fatty acid moiety saturation and length can be performed by methods known in the art. As a non-limiting example gas chromatography (GC) or liquid chromatography-mass spectrometry (HPLC/MS) as taught herein.

Assay for the Determination Lysophospholipase Activity on N-Acyl lysophosphatidylethanolamine (NALPE)

Substrate: 0.6% 18:1 NALPE (N-linoleoyl-(1-oleoyl-glycero-3-phosphoethanolamine) (obtained from Avanti on request or produced according to "Synthesis of N-acyl lysophosphatidylethanolamine (NALPE)"), 0.4% TRITON™-X 100 (Sigma, X-100), and 5 mM $CaCl_2$) were dissolved in 0.05 M HEPES buffer pH 7.0. For pancreatic enzyme 0.003 M Deoxy-cholate was also added.

Assay Procedure:
mL substrate was incubated at 30° C. and added 0.1 mL enzyme solution (approx. 5 TIPU/mL or an enzyme amount corresponding to 2-5% substrate consumed after 10 minutes reaction) in 0.05 M HEPES buffer and incubated with magnetic stirring for 10 minutes. 40 μL 4 M HCl was added to stop the reaction and to protonate the free fatty acids. 1 mL 99% ethanol was added and mixed on a Vortex mixer. 5 mL MTBE (methyl tert-butyl ether) containing 0.5 mg C17:0 fatty acid (margaric acid) was added. The sample was mixed again on a Vortex mixer for 5 sec. and extracted for 30 min on a Rotamix at 25 rpm. The sample was centrifuged at 1520 g for 10 min. One 500 mg amine (NH2)—Bond Elut SPE column (Agilent) was placed on a Bond Elut Vacuum System. The column was conditioned with 8 mL Petroleum-ether. The MTBE phase from the extraction was applied onto the column and eluted with:
1. fraction 8 mL Solvent A: MTBE: 2-propanol, 2:1
2. fraction 8 mL Solvent B: Acetone: Formic acid, 100:2
The solvents were eluted with approx. 0.25 mL/min.

The collected fatty acid fraction (fraction 2) was evaporated to dryness and fatty acid content was analyzed by GLC.

Based on the internal standard C17:0 fatty acid, the amount of C18:1 fatty acid is determined.

Enzyme activity on NALPE is calculated as µmol fatty acid produced per minutes under assay conditions $$\text{Enzyme activity} = 2 \times A \times 1000000 \times D$$

ii. $100 \times MV \times 10 \times 0.1$
Where
A=% C18:1 fatty acids
=mL substrate
1000000=mol conversion to µmol
D=Enzyme dilution factor
MV=molecular weight of C18:1 fatty acid
10=minutes reaction time
c.=mL enzyme added to assay Synthesis of N-acyl lysophosphatidylethanolamine(NALPE)

1.5 gram 1-Oleoyl-2-hydroxy-sn-glycero-3-phosphoethanolamine (18:1 Lyso PE from Avanti) was dissolved in 50 mL Chloroform, and 550 µL triethanolamine was added and covered under nitrogen. The solution was cooled on an ice bath and 1.9 g Linoleic anhydride was added drop wise during stirring. The solution was reacted at 22° C. for 20 hours covered under nitrogen. The crude reaction product was concentrated by evaporation of chloroform under vacuum and purified by column chromatography. The reaction product N-linoleoyl-1-oleoyl-2-hydroxy-sn-glycero-3-phosphoethanolamide (NALPE) was isolated and the structure confirmed by NMR and HPLC/MS.

In one embodiment the phospholipase A2 enzyme which acts on NAPE at the sn2 position according to the present invention may be MAXAPAL®, LYSOMAX® Oil, Pancreatic PLA2, Lipomod 699L from Biocatalysts.

The enzyme that acts on a polar lipid at the sn1 position according to the present invention is one which acts on a polar lipid at the sn1 position as determined using one or both of the following assays: "Assay for determining an enzyme that acts on a polar lipid (a phospholipase) at the sn1 position" and/or "Assay for determining an enzyme that acts on a polar lipid (a galactolipid; MGDG) at the sn1 position".

Assay for determining an enzyme that acts on a polar lipid (a phospholipase) at the sn1 position:

Phospholipase A1 activity (PLA1) was measured using PED-A1 (N-((6-(2,4-DNP)Amino)Hexanoyl)-1-(BODIPY® FL C5)-2-Hexyl-Sn-Glycero-3-hosphoethanolamine (A10070 from ThermoFisher Scientific) as a substrate.

The substrate is specific for PLA1 and is a dye labeled glycerophosphoethanolamine with BODIPY® FL dye-labeled acyl chain at the sn1 position, and dinitrophenyl quencher-modified head group. Quenching efficiency is decreased by cleavage of the BODIPY® FL pentanoic acid substituent at the sn1 position and with an enzyme resistant ether linkage in the sn2 position. The result is a PLA1 dependent increase in fluorescence emission detected at 515 nm.

Procedure:

A "lipid mix" was prepared by mixing 30 µL 10 mM dioleoylphosphatidylcholine in ethanol, 30 µL 10 mM Dioleylphosphatidylglycerol in ethanol and 30 µL 2 mM PED-A1 in DMSO.

Add 5 mL buffer 50 mM Tris HCl, 0.14 mM NaCl and 2 mM CaCl2), pH 7.4 to a 20 mL beaker. Agitate with a magnetic stirrer to form a vortex. Slowly over 1 minute add 50 µL lipid mix into the side of the vortex with a 100 µL-pipette fitted with a narrow orifice gel-loading tip to form the substrate liposome mix.

To a micro titer plate well add 50 µL enzyme sample (or standard or control) and 50 µL substrate liposome mix. Incubate at room temperature for 30 minutes, protected from light. Measure the fluorescence using a micro titer plate reader with excitation at 470 nm and emission at 515 nm.

A calibration curve is constructed based on a number of standard PLA1 solutions of different enzyme concentration from 0 to 10 U/mL. The enzyme standard is a PLA1 (L3295 from Sigma) of known activity. Based on the fluorescence measurement of standard solutions, a calibration curve of fluorescence intensity as a function of enzyme concentration U/mL was constructed. Based on the standard curve the activity of the unknown sample was measured (U/mL).

Assay for determining an enzyme that acts on a polar lipid (a galactolipid; MGDG) at the sn1 position Substrate: 0.6% 1-linoleyl-2-oleyl-3-O—(-D-galactopyranosyl)-sn glycerol (C18:2, C18:1 MGDG)

0.4% TRITON™-X 100 (Sigma, X-100), and 5 mM CaCl$_2$) were dissolved in 0.05 M HEPES buffer pH 7. For pancreatic enzyme 0.003 M Deoxy-cholate was also added.

Assay Procedure:

mL substrate was incubated at 30° C. and added 0.1 mL enzyme solution (approx. 2-5 TIPU/mL or enzyme corresponding to approx. 5% substrate consumed by 10 min reaction) in 0.05 M HEPES buffer and incubated with magnetic stirring for 10 minutes at 30° C. 40 µL 4 M HCl is added to stop the reaction and to protonate the free fatty acids. 1 mL 99% ethanol is added and mixed on a Vortex mixer. 5 mL of MTBE (Methyl tert-butyl ether) containing 0.5 mg C17:0 fatty acid was added. The sample was mixed again on a Wortex mixer for 5 sec. and extracted for 30 min on a Rotamix at 25 rpm. The sample was centrifuged at 1520 g for 10 min.

One 500 mg amine (NH2)—Bond Elut SPE column (Agilent) is placed on a Bond Elut Vacuum System. The column is conditioned with 8 mL Petroleum-ether. The MTBE phase from the extraction is applied onto the column and eluted with:
1. fraction 8 mL Solvent A: MTBE: 2-propanol, 2:1
2. fraction 8 mL Solvent B: Acetone: Formic acid, 100:2
The solvents were eluted with approx. 0.25 mL/min.

The collected fatty acid fraction (fract. 2) is evaporated to dryness and fatty acids are analyzed by GLC. Based on the internal standard C17:0 fatty acid the amount of C18:2 and C18:1 fatty acid is determined.

Enzyme activity is calculated as µmol fatty acid produced per minutes under assay conditions $$\text{Enzyme activity} = 2 \times A \times 1000000 \times D$$

i. $100 \times MV \times 10 \times 0.1$
Where
A=% C18:2 fatty acid+% C18:1 fatty acids
=mL substrate 1000000=mol conversion to μmol
D=Enzyme dilution factor
MV=average molecular weight of C18:2 and C18:1 fatty acids produced
10=minutes reaction time
d.=mL enzyme added to assay
The Enzyme Specificity is Calculated as Relative $sn$1activity=% C18:2×100

1. % C18:2+% C18:1

Relative $sn$2activity=% C18:1×100

2. % C18:2+% C18:1

Synthesis of 1-linoleyl-2-oleyl-3-O—(-D-galactopy-ranosyl)-sn glycerol (C18:2, C18:1 MGDG)

1-linoleyl-2-oleyl-3-O—(-D-galactopyranosyl)-sn glycerol (C18:2, C18:1 MGDG)
1-monolinoleyl-2-hydroxy-3-O—(-D-2',3',4',6'-tetra-O-acetylgalactopyranosyl)-sn-glycerol was synthetized according to Selmair and Koehler (J. Agric. Food Chem. (2008) 56:6691-6700)
1-monolinoleyl-2-hydroxy-3-O-L-D-2',3',4',6'-tetra-O-acetylgalactopyranosyl)-sn-glycerol was isolated and purified by column chromatography to more than 99% purity.
Acylation of the sn2 position of 1-monolinoleyl-2-hydroxy-3-O—(-D-2',3',4',6'-tetra-O-acetylgalactopyranosyl)-sn-glycerol was conducted according to the method of Gaffney and Reese (J. Chem. Soc., Perkin Trans. (2001) 1:192-205.) using oleic acid as acyl donor.
The deacylation of 1-linoleyl-2-oleyl-3-O—(-D-2',3',4', 6'-tetra-O-acetylgalactopyranosyl)-sn-glycerol was conducted with hydrazine in methanol followed by purification by column chromatography, and the structure was confirmed by mass spectrometry and NMR analysis.

In one embodiment, the enzyme that acts on a polar lipid at the sn1 position according to the present invention is one which in the assay entitled "Assay for determining an enzyme that acts on a polar lipid (a phospholipase) at the sn1 position" has at least 20% more relative sn1 activity than relative sn2 activity. In one embodiment, the enzyme that acts on a polar lipid at the sn1 position according to the present invention is one which in the assay entitled "Assay for determining an enzyme that acts on a polar lipid (a phospholipase) at the sn1 position" has at least 50% more relative sn1 activity than relative sn2 activity.

In one embodiment, the enzyme that acts on a polar lipid at the sn1 position according to the present invention is one which in the assay entitled "Assay for determining an enzyme that acts on a polar lipid (a MGDG) as the sn1 position" has at least 20% more relative sn1 activity than relative sn2 activity. In one embodiment, the enzyme that acts on a polar lipid at the sn1 position according to the present invention is one which in the assay entitled "Assay for determining an enzyme that acts on a polar lipid (a MGDG) at the sn1 position" has at least 50% more relative sn1 activity than relative sn2 activity In one embodiment the enzyme that acts on a polar lipid at the sn1 position according to the present invention is one which in a dough can hydrolyse at least 10% of the DGDG using HPTLC analysis of dough lipids.

In one embodiment of the present invention the enzyme that acts on a polar lipid at the sn1 position is an enzyme having phospholipase activity, galactolipase activity, or a combination thereof.

The term "polar lipid" means a polar lipid found in flour (preferably wheat flour). Polar lipids found in wheat flour are defined by Pomeranz, Y. (supra; see FIG. 1). In one embodiment the term "polar lipid" means one or more of the group consisting of: a phospholipid, a galactolipid, or a combination thereof. The phospholipid may be one or more of phosphatidyl choline, N-acyl phosphatidyl ethanolamines, phosphatidyl ethanolamines, phosphatidyl serines or phosphatidyl inositol. In one embodiment preferably the phospholipid may be phosphatidyl choline. The galactolipid may be one or more of digalactosyl diglyceride, ceramide diglycerides, 6-o-acetylsteryl glucosides or ceramide diglucosides. In one embodiment preferably the galactolipid may be digalactosyl diglyceride. In one embodiment the enzyme that acts on a polar lipid at the sn1 position is a phospholipase A1, e.g. has phospholipase A1 activity and may be classified as E.C. 3.1.1.32.

The enzyme that acts on a polar lipid at the sn1 position may act on a galactolipid (e.g. digalactosyldiglyceride (DGDG) or monogalactosyldiglyceride (MGDG). This may be in addition to its phospholipase A1 activity.

Thus in one embodiment the enzyme that acts on a polar lipid at the sn1 position is a galactolipase, e.g. and may be classified as E.C. 3.1.1.26.

In a further embodiment the enzyme that acts on a polar lipid at the sn1 position acts on DGDG at the sn1 position.

The term "acts on" in relation to the enzyme that acts on a polar lipid at the sn1 position as used herein means that the enzyme removes the fatty acid from the sn1 position of a polar lipid (e.g. by hydrolysis) e.g. thus releasing free fatty acid.

The term "preferentially" in relation to the enzyme that acts on a polar lipid at the sn1 position means that the enzyme prefers to catalyse the hydrolysis of a polar lipid at the sn1 position, e.g. compared with catalysing the lysis of the polar lipid at the sn2 position. An enzyme which acts on a polar lipid at the sn1 position can be determined using the assay(s): "Assay for determining an enzyme that acts on a polar lipid (a phospholipase) at the sn1 position" and/or "Assay for the Determination of phospholipase activity and sn1 and sn2 position specificity on PC (phosphatidylcholine)" and/or "Assay for determining an enzyme that acts on a polar lipid (a galactolipid; MGDG) at the sn1 position".

Assay for the Determination of phospholipase activity and sn1 and sn2 position specificity on PC (phosphatidylcholine)

Substrate: 0.6% 16:0-18:1 PC, 1-palmitoyl-2-oleoyl-sn-glycero-3-phosphocholine (Avanti Polar Lipids Inc., Alabaster, Alabama; cat. 850457)

0.4% TRITON™-X 100 (Sigma, X-100), and 5 mM $CaCl_2$) were dissolved in 0.05 M HEPES buffer pH 7.

For pancreatic enzyme 0.003 M Deoxycholate was also added.

Assay Procedure:

mL substrate was incubated at 30° C. and added 0.1 mL enzyme solution (approx. 2-5 TIPU/mL or an enzyme amount corresponding to 2-5% substrate consumed after 10 minutes reaction) in 0.05 M HEPES buffer and incubated with magnetic stirring for 10 minutes at 30° C. 40 μL 4 M HCl is added to stop the reaction and to protonate the free fatty acids. 1 mL 99% ethanol is added and mixed on a Vortex mixer. 5 mL MTBE (methyl tert-butyl ether) containing 0.5 mg C17:0 fatty acid (margaric acid) was added. The sample was mixed again on a Vortex mixer for 5 sec. and extracted for 30 minutes on a Rotamix at 25 rpm. The sample was centrifuged at 1520 g for 10 min.

One 500 mg amine ($NH_2$)—Bond Elut SPE column (Agilent) is placed on a Bond Elut Vacuum System. The column is conditioned with 8 mL Petroleum-ether. The MTBE phase from the extraction is applied onto the column and eluted with:
1. fraction 8 mL Solvent A: MTBE: 2-propanol, 2:1
2. fraction 8 mL Solvent B: Acetone: Formic acid, 100:2
The solvents were eluted with approx. 0.25 mL/min.

The collected fatty acid fraction (fract. 2) is evaporated to dryness and fatty acids are analyzed by GLC. Based on the internal standard C17:0 fatty acid the amount of C16:0 and C18:1 fatty acid is determined.

Enzyme activity is calculated as µmol fatty acid produced per minutes under assay conditions $$\text{Enzyme activity} = 2 \times A \times 1000000 \times D$$

ii. 100×MV×10×0.1
Where
A=% C16:0 fatty acid+% C18:1 fatty acids
=mL substrate
1000000=mol conversion to µmol
D=Enzyme dilution factor
MV=average molecular weight of C16:0 and C18:1 fatty acids produced
10=minutes reaction time
e.=mL enzyme added to assay
The Enzyme Specificity is Calculated as $$\text{Relative } PLA1 \text{ activity} = \% C16:0 \times 100$$

1. % C16:0+% C18:1

$$\text{Relative } PLA2 \text{ activity} = \% C18:1 \times 100$$

2. % C16:0+% C18:1

The term "preferentially" in relation to the enzyme that acts on a polar lipid at the sn1 position means that the enzyme prefers to catalyse the hydrolysis of a polar lipid at the sn1 position, e.g. compared with catalysing the lysis of the polar lipid at the sn2 position. An enzyme which acts on a polar lipid at the sn1 position can be determined using the assay(s): "Assay for determining an enzyme that acts on a polar lipid (a phospholipase) at the sn1 position" and/or "Assay for the Determination of phospholipase activity and sn1 and sn2 position specificity on PC (phosphatidylcholine)" and/or "Assay for determining an enzyme that acts on a polar lipid (a galactolipid; MGDG) at the sn1 position".

An enzyme that preferentially acts on polar lipids at the sn1 position means that the relative PLA1/sn1 activity when determined using the "Assay for the Determination of phospholipase activity and sn1 and sn2 position specificity on PC (phosphatidylcholine)" and/or "Assay for determining an enzyme that acts on a polar lipid (a galactolipid; MGDG) at the sn1 position" would be at least 60%.

In one embodiment an enzyme that preferentially acts on polar lipids at the sn1 position means that the relative PLA1/sn1 activity when determined using the "Assay for the Determination of phospholipase activity and sn1 and sn2 position specificity on PC (phosphatidylcholine)" and/or "Assay for determining an enzyme that acts on a polar lipid (a galactolipid; MGDG) at the sn1 position" would be at least 70%.

The term "specifically" in relation to the enzyme that acts on a polar lipid at the sn1 position means that the enzyme will catalyse only the hydrolysis of a polar lipid at the sn1 position.

An enzyme that specifically acts on polar lipids at the sn1 position means that the enzyme has at least 60% (suitably at least 70%) relative PLA1/sn1 activity when determined using the "Assay for the Determination of phospholipase activity and sn1 and sn2 position specificity on PC (phosphatidylcholine)" and/or "Assay for determining an enzyme that acts on a polar lipid (a galactolipid; MGDG) at the sn1 position".

According to one embodiment the enzyme that acts on a polar lipid at the sn1 position may include the enzyme as taught in WO02/03805 (which is incorporated herein by reference). In one embodiment the enzyme that acts on a polar lipid at the sn1 position includes POWERBAKE® 4080, POWERBAKE® 4090, PANAMORE®, LIPOPAN F™, and LIPOPAN EXTRA™.

In one embodiment the enzyme that acts on a polar lipid at the sn1 position may be a phospholipase A1 from *Fusarium oxysporum* (e.g. LIPOPAN F™). In one embodiment the phospholipase A1 from *Fusarium oxysporum* may be the enzyme taught in WO98/26057— which is incorporated herein by reference.

In one embodiment the enzyme that acts on a polar lipid at the sn1 position according to the present invention is one which has at least 60% sequence identity, more preferably at least 70%, at least 80%, at least 90%, at least 95% or 100% identity to SEQ ID NO: 1.

Preferably the enzyme that acts on polar lipid at the sn1 position has low activity on NAPE.

One advantage of the present invention is the use of a combination of a phospholipase A2 enzyme which acts on N-acyl phosphatidyl ethanolamine (NAPE) at the sn2 position and an enzyme that acts on a polar lipid at the sn1 position.

The fatty acid composition of phospholipids and galactolipids at the sn1 and sn2 positions differs significantly, both in fatty acid length and saturation levels.

It has surprisingly been found that by combining enzymes that act either at the sn1 position or the sn2 position a beneficial combination of polar lipids (e.g. lysophospholipids and lysogalactolipids (e.g. MGMG or DGMG)) can be obtained which provides significant benefits to the dough and products obtained from that dough, e.g. by cooking such as baking, steaming, boiling or frying.

Even in NAPE the fatty acids present at the sn1 or sn2 positions are quite different, with generally speaking more unsaturated fatty acids found in sn2 position. A phospholipase A1 may hydrolyse NAPE at the sn-1 position to produce 2-NALPE, e.g. with the fatty acid in the sn-2 position (see Structural Analysis of Wheat Flour Glycerolipids. Lipids, Vol. 6, No. 10 p. 768-776).

Therefore, the invention relates to the impact of lysing (e.g. hydrolysing) NAPE at the sn2 position in combination with modifying a polar lipid (e.g. further polar lipid) with an enzyme that acts at the sn1 position.

We are the first to show the importance of selectively lysing (e.g. hydrolysing) NAPE and a further polar lipid.

In accordance with the present invention the phospholipase A2 enzyme and the enzyme that acts on polar lipids are admixed to the dough components in effective amounts that result in an increase of the specific volume of the baked product that is at least 10%, relative to a baked product made under identical conditions except for the addition of the claimed enzymes.

In accordance with the present invention a phospholipase A2 enzyme which acts on N-acyl phosphatidyl ethanolamine at the sn2 position and an enzyme that acts on a polar lipid at the sn1 position are admixed to the dough components in effective amounts that result in an increased softness of the baked product that is at least 5%, preferably at least 10%, more preferably at least 20%, most preferably at least 30% relative to a baked product made under identical conditions except for the addition of the claimed enzymes.

The terms "improved softness" and "increased softness" as used herein are considered synonymous and may refer to a reduction in force per specific volume in a baked product.

Suitably a food enzyme composition is considered to increase monogalactosylmonoglyceride content in a dough or baked product when the lipid components are extracted from the dough or baked product (e.g. and subject to gas chromatography (GC) or liquid chromatography-mass spectrometry (HPLC/MS) analysis) or HPTLC analysis, showing more than about 0.005% w/w increase in monogalactosylmonoglyceride base on dry dough weight, suitably more that 0.01% w/w (momogalactosylmonoglyceride based on dry dough weight), suitably more than 0.025% w/w increase, suitably more than 0.05% w/w increase, suitably more than 0.075% w/w increase in monogalactosylmonoglyceride content based on dry dough weight in comparison to an identical dough or baked product where the enzyme has not been added.

Suitably a food enzyme composition is considered to increase monogalactosylmonoglyceride content in a dough or baked product when the lipid components are extracted from the dough or baked product (e.g. and subject to gas chromatography (GC) or liquid chromatography-mass spectrometry (HPLC/MS) analysis or HPTLC analysis, showing between about 0.005 and 0.1% w/w increase (based on dough dry dough) in monogalactosylmonoglyceride content in comparison to an identical dough or baked product where the enzyme has not been added.

According to the present invention a food enzyme composition is considered to decrease digalactosyldiglyceride content in a dough or baked product when the lipid components are extracted from the dough or baked product (e.g. and subject to gas chromatography (GC) or liquid chromatography-mass spectrometry (HPLC/MS) analysis or HPTLC analysis), showing a reduction of at least 5%, preferably at least 10%, more preferably at least 20%, more preferably at least 30%, suitably at least 40% in digalactosyldiglyceride content in comparison to an identical dough or baked product where the food enzyme composition has not been admixed.

According to the present invention a food enzyme composition is considered to decrease digalactosyldiglyceride content in a dough or baked product. It is analyzed when the lipid components are extracted from the fully proofed dough or baked product (e.g. and subject to gas chromatography (GC) or liquid chromatography-mass spectrometry (HPLC/MS) analysis or HPTLC analysis), showing a reduction of between about 5% and 50% in relative digalactosyldiglyceride content (e.g. about 0.01 to 0.1% w/w DGDG based on dry dough) in comparison to an identical dough or baked product where the food enzyme composition has not been admixed.

In one embodiment the phospholipase A2 enzyme of the present invention is present at a concentration of between 100-7500 ePLU/kg flour. In one embodiment the phospholipase A2 enzyme is dosed at 150-2000 ePLU/kg flour.

In one embodiment of the enzyme that acts on a polar lipid at the sn1 position of the present invention is present at a concentration of between 50-2000 TIPU/kg flour. In one embodiment the enzyme that acts on a polar lipid at the sn1 position of the present invention is dosed at 200-800 TIPU/kg flour.

ePLU Assay:

The phospholipase A2 enzyme activity (ePLU) may be determined using the following assay using egg yolk as substrate.

The assay is conducted according to Food Chemical Codex (FCC, 8ed., Appendix 5 p. 1328) Substrate:

To 44 g egg yolk (1 beaker with 2 egg yolk) was added 200 mL water and homogenized with an Ultra Turrax mixer. 10 mL 0.3 M Calcium chloride was added. 10 mL substrate was transferred to titration glass and 10 mL water and 5 mL 0.016 M Sodium Deoxycholate was added. The substrate was incubated at 40° C. and pH was adjusted with 0.05 M NaOH to pH 8 using pH stat titrator. 0.1 mL enzyme was added and titration data was collected for 5 min. The titrant was 0.05 M NaOH. The slope for titrant consumption as a function of time (70 sec to 170 sec) was used to calculate the activity (ePLU) as µmol fatty acids released per minutes under assay conditions.

TIPU Assay:

Phospholipase activity (TIPU) may be determined using the following assay:

Substrate: 0.6% L-a Phosphatidylcholine 95% Plant (Avanti, cat. #441601), 0.4% TRITON™-X 100 (Sigma X-100), and 5 mM $CaCl_2$) were dissolved in 0.05 M HEPES buffer pH 7.

Assay Procedure:

Samples, calibration sample, and control sample were diluted in 10 mM HEPES pH 7.0 containing 0.1% TRITON™ X-100. Analysis was carried out using a Konelab Autoanalyzer (Thermo, Finland). The assay was run at 30° C. 34 µL substrate was thermostatted for 180 seconds at 30° C., before 4 µL of enzyme sample was added. Enzymation lasted 600 sec. The amount of free fatty acid liberated during enzymation was measured using the NEFA kit obtained from WakoChemicals GmbH, Germany).

This assay kit is composed of two reagents

NEFA-HR(1):

50 mM Phosphate buffer pH 7.0 containing 0.53 U/mL Acyl-CoA Synthase(ACS)

0.31 mM coenzyme A(CoA)

4.3 mM adenosine 5-triphosphate disodium salt (ATP)

1.5 mM 4-amino-antipyrine (4-AA)

2.6 U/mL Ascorbate oxidase (AOD)

0.062% Sodium azide

NEFA-HR(2):

2.4 mM 3-Methyl-N-Ethyl-N-(E-Hydroxyethyl)-Aniline (MEHA)

12 U/mL Acyl-CoA oxidase (ACOD)

14 U/mL Peroxidase (POD)

After enzymation 113 µL NEFA-HR(1) was added and the mixture was incubated for 300 sec. Afterwards 56 µL NEFA-HR(2) was added and the mixture was incubated for 300 sec. OD 520 nm was then measured. Enzyme activity (µmol FFA/min·mL) was calculated based on a calibration curve made form oleic acid. Enzyme activity TIPU pH 7 was calculated as micromole fatty acid produced per minute under assay conditions.

A flour dough may not contain sufficient amounts of all of the lipid substrates for the composition of the invention. It is therefore within the scope of the invention to supplement the dough with at least one of a galactolipid, a phospholipid or a combination thereof to provide sufficient substrates for the enzyme(s). It will be appreciated that the expression "sufficient substrate" implies that none of the lipid substrates is limiting for obtaining a dough improving or baked product improving effect as described above.

The supplementary lipid substrate for the enzyme of the invention may be a polar lipid. In this connection, a particularly useful lipid is an oil or a fat derived from cereals such as oat oil. Oat oil typically contains, in addition to triglycerides, 5-25% phospholipids and 5-12% glycolipids. Oat oil can be fractionated to yield fractions having a high content of polar lipids.

Thus, it is contemplated that one or more phospholipids can be added to the dough. In this connection, useful phospholipids include phosphatidylethanolamine (PE), phosphatidylinositol (PI), phosphatidylglycerol (PG), and phosphatidylcholine (PC).

In one embodiment the composition of the present invention further comprises lecithin.

In a further embodiment the composition for use according to the present invention further comprises lecithin.

In another embodiment the method of the present invention further comprises admixing lecithin.

In one embodiment the lecithin of the present invention is soya-derived lecithin.

In another embodiment the lecithin of the present invention has been enzymatically modified.

Suitably the lecithin of the present invention has been enzymatically modified by an enzyme with phospholipase A2 activity.

Preferably the lecithin of the present invention has been modified by a phospholipase A2 that is capable of acting at the sn2 position of N-acetyl phosphatidylethanolamine.

The present invention yet further provides the use of a phospholipase A2 enzyme which acts on N-acyl phosphatidyl ethanolamine at the sn2 position and an enzyme that acts on a polar lipid at the sn1 position in the manufacture of a dough or a baked product for improving the specific volume of a baked product; dough characteristics (such as dough development; dough extensibility); improving crust crispiness of a baked product; improving the crumb structure (such as improving crumb pore size of a baked product or improving crumb pore homogeneity of a baked product); improving softness (such as improving softness of a baked product); improving the oven spring of a baked product; increasing N-acyl lysophosphatidyl ethanolamine in the dough and/or baked product (preferably increasing N-acyl lysophosphatidyl ethanolamine with a fatty acid moiety containing 14-20 carbon atoms, preferably increasing N-acyl lysophosphatidyl ethanolamine with a saturated fatty acid moiety containing 14-20 carbon atoms); increasing a lyso-phospholipid in the dough and/or baked product; increasing a digalactosylmonoglyceride and/or monogalactosylmonoglyceride in the dough and/or baked product; increasing N-acyl lysophosphatidyl ethanolamine together with increasing a lyso-phospholipid and/or a digalactosylmonoglyceride and/or monogalactosylmonoglyceride in the dough and/or baked product.

The present invention may further advantageously provide a method for obtaining a baked product having improved quality characteristics (such as improved specific volume, improved crust crispiness of a baked product; improved crumb structure (such as improved crumb pore size of a baked product or improved crumb pore homogeneity of a baked product); improved softness (such as improved softness of a baked product); improved capping of a baked product; improved oven spring of a baked product).

Accordingly, in one embodiment the method of the present invention comprises as a further step that the dough is baked to obtain a baked product. One particularly desired property of baked bread products is a high specific volume as defined in the examples. Accordingly, the addition of the enzymes of the invention preferably results in an increase of the specific volume of the baked product that is at least 10%, relative to a baked product made under identical conditions except that the enzyme is not added. More preferably, the increase of the specific volume is at least 20% such as at least 30%, e.g. at least 40%.

It is known in the art that enzymes other than lipases may contribute to improved dough properties and quality of baked products. It is within the scope of the invention that, in addition to the composition of the invention, at least one further enzyme may be added. Such further enzymes include a lipase, starch degrading enzyme (e.g. an amylase or an amyloglucosidase), a hemicellulase (e.g. xylanase), a cellulase, an oxidoreductase (e.g. a glucose oxidase, such as hexose oxidase), a lipid acyltransferase, a debranching enzyme (e.g. a pullulanase), a lactase and a protease.

According to another embodiment the claimed method comprises a further step wherein a further enzyme is admixed to the dough components.

Specific Volume

Specific volume in baked products can be defined as the volume of the product divided by its weight. (g/mL or g/ccm)

The present invention relates to improving the specific volume of a baked product.

Dough Characteristics

The present invention may relate to improving dough characteristic, such as dough development; dough extensibility. The present invention does not negatively impact dough stickiness.

These may be measured in dough as follows:

| Evaluation Dough | Evaluation method | Lowest score = 1 | Highest score = 10 |
|---|---|---|---|
| Dough development after mixing | Extend dough with fingers | Dough cannot be stretched without breaking | Dough can be stretched obtaining papery thin dough without breakage |
| Stickiness after mixing | Cut a big slit in all dough, open the dough, touch the cut dough surface with fingers | Dry surface. The dough slips your fingers | The dough sticks to your fingers |
| Extensibility after resting | Extend dough with fingers | Dough cannot be stretched without breaking | Dough can be stretched obtaining papery thin dough without breakage |

| Evaluation Dough | Evaluation method | Lowest score = 1 | Highest score = 10 |
|---|---|---|---|
| Stickiness after resting | Cut a big slit in all dough, open the dough, touch the cut dough surface with fingers | Dry surface. The dough slips your fingers | The dough sticks to your fingers |

Crust Crispiness

The present invention may relate to improving crust crispiness of a baked product.

This may be measured in baked products, e.g. bread or bread rolls as follows:

| Evaluation | Evaluation method | Lowest score = 1 | Highest score = 10 |
|---|---|---|---|
| Crispiness of crust | Fracture crust using several fingers | Leathery crust | Crisp crust |

Crumb Structure

The present invention may relate to improving the crumb structure (such as improving crumb pore size of a baked product or improving crumb pore homogeneity of a baked product).

These may be measured in baked products, e.g. bread or bread rolls as follows:

| Evaluation | Evaluation method | Lowest score = 1 | Highest score = 10 |
|---|---|---|---|
| Crumb pore size | Visual evaluation of sliced bread, size of gas bubbles in crumb | Open crumb, big gas bubbles | Fine crumb, small gas bubbles |
| Crumb pore homogeneity | Visual evaluation of sliced bread, homogeneity of gas bubbles | Big variation in sizes of gas bubbles | Constant gas bubble size |

Softness

The present invention may relate to improving softness (such as improving softness of a baked product).

Softness may also be measured by any method known in the art.

This may be measured in baked products, e.g. bread or bread rolls as follows:

| Evaluation | Evaluation method |
|---|---|
| Softness | Force per specific volume required to compress the complete baked product until certain deformation. Data shown in force/specific volume. A decreased force indicates softer bread. |

In one embodiment the softness (or hardness) of bread slices was determined from a texture profile analysis (TPA) using a Texture analyser TAXTplus from Stable Microsystems. By way of example a 35 mm metal probe may be used to measure softness on days 1 (D1) and 3 (D3).

Capping

The present invention does not negatively affect capping of a baked product;

One common baking characteristic, known as "capping", is commonly seen and is particularly undesirable. Capping occurs when the top has set (i.e., hardened), and then this top is pushed up, allowing batter from the interior of the baked product, e.g. muffin or roll, to ooze out to the side. The result is an undesirable baked product, e.g. muffin or roll.

Capping was subjectively evaluated by examining the baked product and the amount of capping observed was assigned a qualitative number.

This may be measured in baked products as follows:

| Evaluation | Evaluation method | Lowest score = 1 | Highest score = 10 |
|---|---|---|---|
| Capping/ Hole under the crust | Visual evaluation of vertical cut surface | A very large hole directly under the crust. | No separation between crust and crumb. |

Oven Spring

The present invention may relate to improving the oven spring of a baked product;

The term "oven spring" as used herein means the rapid increase in volume (rising) of baked products, e.g. bread when they are placed into a hot oven.

This may be measured in baked products as follows:

| Evaluation | Evaluation method | Lowest score = 1 | Highest score = 10 |
|---|---|---|---|
| Oven spring/Energy | Visual evaluation amount of energy in the product | No energy | High level of energy |

Increasing or Improving

The terms increasing or improving as used herein means increasing or improving compared with the same dough or product obtainable from said dough (e.g. a baked product) but without addition of the enzymes in accordance with the present invention.

Additional technical effects of the present invention include increasing N-acyl lysophosphatidyl ethanolamine in the dough and/or baked product (preferably increasing N-acyl lysophosphatidyl ethanolamine with a fatty acid moiety containing 14-20 carbon atoms, preferably increasing N-acyl lysophosphatidyl ethanolamine with a saturated fatty acid moiety containing 14-20 carbon atoms); increasing a lyso-phospholipid in the dough and/or baked product; increasing a digalactosylmonoglyceride and/or monogalactosylmonoglyceride in the dough and/or baked product.

In a preferred embodiment the present invention relates to increasing N-acyl lysophosphatidyl ethanolamine (NALPE) (preferably 1-NALPE) together with increasing a lyso-phospholipid and/or a digalactosylmonoglyceride and/or monogalactosylmonoglyceride in the dough and/or baked product.

Synergy/Synergistic Effect

For the first time the present inventors have shown the synergistic effects provided by the combination of a phospholipase A2 enzyme which is capable of acting on NAPE at the sn2 position and an enzyme that acts on a polar lipid at the sn1 position in a foodstuff, e.g. a dough or a baked product.

The terms "synergy" or "synergistic effect" means an increase in the effect (e.g. bread volume) which is more than the increase obtained from each enzyme when used individually or separately, in the same dosage.

Food or Foodstuff

The method, uses or compositions of the present invention may be used in the preparation of a foodstuff. Here, the term "foodstuff" is used in a broad sense—and covers foodstuff for humans as well as foodstuffs for animals (i.e. a feedstuffs). In a preferred aspect, the foodstuff is for human consumption.

In the present invention the term "dough component" means any one of flour (e.g. cereal flour, preferably wheat flour), water or yeast or any composition comprising one or more of flour, water and/or yeast.

Preferably the enzyme(s) of the present invention are admixed with a dough component.

Preferably the enzyme(s) of the present invention are admixed with flour or with a composition comprising flour.

In one embodiment the foodstuff is a dough or a product produced from the dough, e.g. by cooking, such as by baking or steaming, boiling or frying.

In one embodiment the baked product is obtainable (preferably obtained) from a dough.

In one embodiment the steamed product is obtainable (preferably obtained) from a dough.

In one embodiment the boiled product is obtainable (preferably obtained) from a dough.

In one embodiment the fried product is obtainable (preferably obtained) from a dough.

In one embodiment the foodstuff is a baked product.
In one embodiment the foodstuff is a steamed product.
In one embodiment the foodstuff is a boiled product.
In one embodiment the foodstuff is a fried product.

The method, uses or compositions of the present invention can be used in the preparation of a dough or a product produced from the dough, e.g. by cooking, such as by baking, steaming, boiling or frying.

Preferably the baked product is produced by baking a dough produced in accordance with the present invention.

Preferably the boiled product is produced by boiling a dough produced in accordance with the present invention.

Preferably the steamed product is produced by steaming a dough produced in accordance with the present invention.

Preferably the fried product is produced by frying a dough produced in accordance with the present invention.

For certain aspects, preferably the foodstuff is a baked product, such as bread (e.g. white, whole-meal or rye bread; typically in the form of loaves or rolls, French baguette-type bread, pita bread, flatbreads, crisp bread or pizza bread), tortillas, pancakes, muffins, pie crusts, pastry, Danish pastry, cakes, biscuits, or cookies.

In one aspect the foodstuff is a steamed product, such as a steamed bread, dumplings.

In one aspect the foodstuff is a boiled product, such as noodles or pasta.

In one aspect the foodstuff is a fried product, such as a doughnut.

A "food enzyme composition" as defined herein may be any composition suitable for addition to a dough or suitable for admixing with a dough component.

As a non-limiting example food products of the present invention include baked products and dough products.

The term "dough" as used herein means a thick, malleable mixture of flour and liquid (e.g. water). The dough may include yeast or other leavening agents. The dough may further comprise other dough components such as a fat or a flavouring(s) or salt or sugar.

The dough according to the present invention may be made from one or more of the flours selected from: wheat flour, maize flour, rice flour, rye flour, legume flour, almond flour or other cereal flours.

In one embodiment the dough is made from wheat flour.

The method and uses of the present invention may be part of any bread making process. The composition of the present invention may be used in any bread making process. By way of example the bread making process may be one or more processes selected from the group consisting of: sponge-and-dough; straight; no-time and continuous bread making.

The "Sponge-and-Dough" Method

Without being bound by theory the sponge-and-dough mixing method may consist of two distinct stages, a sponge stage and a dough stage. In the first stage (sponge stage) a sponge is made and allowed to ferment for a period of time; and in the second stage (dough stage) the sponge is added to the final dough ingredients creating a total formula. Other terms for "sponge" include yeast starter or yeast pre-ferment. In French baking the sponge and dough method may be known as levain-levure.

In the first stage, the mixture, called the sponge, may contain about one-third to three-quarters of the flour, the yeast, yeast food (e.g. sugar), and malt, and enough water to make a stiff dough or a more liquid brew. Shortening may be added at this stage, although it is usually added later, and one-third to three-quarters of the salt may be added to control fermentation.

The sponge may be mixed in any suitable mixing device, suitably with temperature control. Suitably this may be a large, horizontal dough mixer, processing about one ton per batch, and is optionally constructed with heat-exchange jackets, allowing temperature control.

The objectives of mixing are a nearly homogeneous blend of the ingredients and "developing" of the dough by formation of the gluten into elongated and interlaced protein network that will form the basic structure of the loaf. Because intense shearing actions must be avoided, the usual dough mixer has several horizontal bars, oriented parallel to the body of the mixer, rotating slowly at 35 to 75 revolutions per minute, stretching and kneading the dough by their action. A typical mixing cycle would be about 12 minutes.

The mixed sponge is dumped into a trough, a shallow rectangular metal tank on wheels, and placed in an area of controlled temperature and humidity (e.g., 27° C. and 75% relative humidity), where it is fermented until it begins to decline in volume. The time required for this process, called the drop or break, depends on such variables as temperature, type of flour, amount of yeast, absorption, and amount of malt, which are frequently adjusted to produce a drop in about three to five hours.

At the second, or dough, stage, the sponge is returned to the mixer, and the remaining ingredients are added. The dough is developed to an optimum consistency then either returned to the fermentation room or allowed "floor time" for further maturation.

In one embodiment a phospholipase A2 enzyme which acts on N-acyl phosphatidyl ethanolamine at the sn2 position and an enzyme that acts on a polar lipid at the sn1 position may be added at either the sponge stage or the dough stage, preferably the sponge stage. These may be added simultaneously or sequentially.

In another embodiment the phospholipase A2 enzyme which acts on N-acyl phosphatidyl ethanolamine at the sn2 position may be added at the sponge stage (e.g. during admixing the flour and other dough components). Alternatively or in addition, the enzyme that acts on a polar lipid at the sn1 position may be added to the dough stage (e.g. during mixing).

In one embodiment the phospholipase A2 enzyme which is capable of acting on NAPE is added to a sponge and the enzyme that acts on a polar lipid at the sn1 position is added to the dough.

In one embodiment a lecithin may additionally be added, preferably soya-based lecithin, at the sponge stage (e.g. during admixing the flour and other dough components). Suitably the lecithin may be added together with at least a phospholipase A2 enzyme which acts on N-acyl phosphatidyl ethanolamine at the sn2 position. Suitably the lecithin may be an enzymatically modified lecithin. In one embodiment lecithin may be enzymatically modified by an enzyme with phospholipase A2 activity (preferably the lecithin may be enzymatically modified by a phospholipase A2 that acts on N-acyl phosphatidyl ethanolamine at the sn2 position).

In one embodiment the phospholipase A2 or a portion thereof is added during sponge stage.

The "Straight dough" method

The straight dough method may be a single-mix process of making bread. All components (e.g. ingredients) for making the dough are all placed together and combined in one kneading or mixing session. After mixing, a bulk fermentation rest occurs before division.

In one embodiment a phospholipase A2 enzyme which acts on N-acyl phosphatidyl ethanolamine at the sn2 position and an enzyme that acts on a polar lipid at the sn1 position may be admixed with the dough components. These may be added simultaneously or sequentially.

In one embodiment a lecithin may additionally be added, preferably soya-based lecithin. Suitably the lecithin may be an enzymatically modified lecithin. In one embodiment lecithin may be enzymatically modified by an enzyme with phospholipase A2 activity (preferably the lecithin may be enzymatically modified by a phospholipase A2 that acts on N-acyl phosphatidyl ethanolamine at the sn2 position).

The "No-Time" Method

The "no-time" method is a special subset of the straight dough method. As a non-limiting example increased amounts of yeast and fast-acting oxidants such as ascorbic acid and azodicarbonamide enable the elimination of most of the straight dough bulk fermentation period.

Continuous Bread Making

Many steps in conventional dough preparation and makeup have been fully automated, but none of the processes is truly continuous. In continuous systems, the dough is handled without interruption from the time the ingredients are mixed until it is deposited in the pan. The initial fermentation process is still essentially a batch procedure, but in the continuous bread-making line the traditional sponge is replaced by a liquid pre-ferment, called the broth or brew. The brew consists of a mixture of water, yeast, sugar, and portions of the flour and other ingredients, fermented for a few hours before being mixed into the dough.

After the brew has finished fermenting, it is fed along with the dry ingredients into a mixing device, which mixes all ingredients into a homogeneous mass. The batter like material passes through a dough pump regulating the flow and delivering the mixture to a developing apparatus, where kneading work is applied. The developer is the key equipment in the continuous line. Processing of about 50 kilograms (100 pounds) can occur each 90 seconds, it changes the batter from a fluid mass having no organized structure, little extensibility, and inadequate gas retention to a smooth, elastic, film-forming dough. The dough then moves out of the developer into a metering device that constantly extrudes the dough and intermittently severs a loaf-size piece, which falls into a pan passing beneath.

In one embodiment a phospholipase A2 enzyme which acts on N-acyl phosphatidyl ethanolamine at the sn2 position and an enzyme that acts on a polar lipid at the sn1 position may be added to the liquid pre-ferment or to the dough, e.g. after fermentation and during mixing of the dough. These may be added simultaneously or sequentially.

In another embodiment the phospholipase A2 enzyme which acts on N-acyl phosphatidyl ethanolamine at the sn2 position may be added to the liquid pre-ferment. Alternatively or in addition, the enzyme that acts on a polar lipid at the sn1 position may be added to the dough, e.g. after fermentation and during mixing of the dough.

In one embodiment a lecithin may additionally be added, preferably soya-based lecithin, at either the pre-ferment stage or to the dough, e.g. after fermentation and during mixing of the dough. Suitably the lecithin may be added together with at least a phospholipase A2 enzyme which acts on N-acyl phosphatidyl ethanolamine at the sn2 position. Suitably the lecithin may be an enzymatically modified lecithin. In one embodiment lecithin may be enzymatically modified by an enzyme with phospholipase A2 activity (preferably the lecithin may be enzymatically modified by a phospholipase A2 that acts on N-acyl phosphatidyl ethanolamine at the sn2 position).

Unless defined otherwise, all technical and scientific terms used herein have the same meaning as commonly understood by one of ordinary skill in the art to which this disclosure belongs. Singleton, et al., DICTIONARY OF MICROBIOLOGY AND MOLECULAR BIOLOGY, 20 ED., John Wiley and Sons, New York (1994), and Hale & Marham, THE HARPER COLLINS DICTIONARY OF BIOLOGY, Harper Perennial, NY (1991) provide one of skill with a general dictionary of many of the terms used in this disclosure.

This disclosure is not limited by the exemplary methods and materials disclosed herein, and any methods and materials similar or equivalent to those described herein can be used in the practice or testing of embodiments of this disclosure. Numeric ranges are inclusive of the numbers defining the range. Unless otherwise indicated, any nucleic acid sequences are written left to right in 5' to 3' orientation; amino acid sequences are written left to right in amino to carboxy orientation, respectively.

The headings provided herein are not limitations of the various aspects or embodiments of this disclosure which can be made by reference to the specification as a whole. Accordingly, the terms defined immediately below are more fully defined by reference to the specification as a whole.

Amino acids are referred to herein using the name of the amino acid, the three letter abbreviation or the single letter abbreviation.

The term "protein", as used herein, includes proteins, polypeptides, and peptides.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The terms "protein" and "polypeptide" are used interchangeably herein. In the present disclosure and claims, the conventional one-letter and three-letter codes for amino acid residues may be used. The 3-letter code for amino acids as defined in conformity with the IUPACIUB Joint Commission on Biochemical Nomenclature (JCBN). It is also understood that a polypeptide may be coded for by more than one nucleotide sequence due to the degeneracy of the genetic code.

Other definitions of terms may appear throughout the specification. Before the exemplary embodiments are described in more detail, it is to understand that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within this disclosure. The upper and lower limits of these smaller ranges may independently be included or excluded in the range, and each range where either, neither or both limits are included in the smaller ranges is also encompassed within this disclosure, subject to any specifically excluded limit in the stated range. Where the stated range includes one or both of the limits, ranges excluding either or both of those included limits are also included in this disclosure.

It must be noted that as used herein and in the appended claims, the singular forms "a", "an", and "the" include plural referents unless the context clearly dictates otherwise. Thus, for example, reference to "an enzyme" includes a plurality of such candidate agents and reference to "dough component" includes reference to one or more dough components and equivalents thereof known to those skilled in the art, and so forth.

The publications discussed herein are provided solely for their disclosure prior to the filing date of the present application. Nothing herein is to be construed as an admission that such publications constitute prior art to the claims appended hereto.

The invention will now be described, by way of example only, with reference to the following Examples.

EXAMPLES

Materials and Methods:
Materials:

A phospholipase A2 enzyme which acts on N-acyl phosphatidyl ethanolamine specifically at the sn2 position—MAXAPAL®, #4313, commercially available from DSM, NL (10000 ePLU/mL)

LIPOMOD™ 699L is a phospholipase A2 enzyme which acts on NAPE at the sn2 position, this is a pancreas phospholipase A2, commercially available from Biocatalysts (12000 ePLU/mL).

POWERBAKE® 4080, an enzyme that acts on a polar lipid at the sn1 position (commercially available from DuPont)— this enzyme is known to have both galactolipase and phospholipase activity (10000 TIPU/g) and has the amino acid sequence as shown in SEQ ID NO: 1.

POWERBAKE® 4090, an enzyme that acts on a polar lipid at the sn1 position (commercially available from DuPont)— this enzyme is known to have both galactolipase and phospholipase activity (15,500 TIPU/g) and has the amino acid sequence as shown in SEQ ID NO: 1 (POWERBAKE® 4090 is the same enzyme as POWERBAKE® 4080, but in POWERBAKE® 4090 the enzyme is more concentrated).

LYSOMAX® Oil, Glycerophospholipid Cholesterol Acyltransferase (GCAT), otherwise known as a lipid acyltransferase (SEQ ID NO: 2; commercially available from Dupont). This enzyme can act on N-acyl phosphatidyl ethanolamine at the sn2 position. Enzyme activity 1000 TIPU/g.

LIPOPAN™ F is an enzyme that acts on a polar lipid at the sn1 position, and is referred to as a phospholipase A1. This enzyme is commercially available from Novozymes DK (18500 TIPU/g).

PANAMORE® Golden Conc., #4240, is an enzyme that acts on a polar lipid at the sn1 position and is referred to as a phospholipase A1. This enzyme is commercially available from DSM, NL (29000 TIPU/g).

SUREBAKE® 800, Hexose oxidase (HOX) from Dupont.

TLC Analysis
Apparatus:
Applicator: Automatic TLC Sampler 4, CAMAG ADC2 Automatic developing chamber programmed to an elution time of 7 cm.

HPTLC plate: 10×20 cm Silica plates no. 1.05641.0001 from Merck. Activated on a CAMAG TLC Plate Heater III for 10 minutes at 160° C. before use.

Development: the HPTLC Silica plate was dried on a CAMAG TLC Plate Heater III for 10 minutes at 160° C., cooled, and dipped in 6% cupric acetate in 16% $H_3PO_4$. Additionally dried for 6 minutes at 160° C. and evaluated directly.

Analysis of Dough Lipids:
5 µL of the dough lipid (from 200 mg dry dough) sample dissolved in 0.5 mL heptane:isopropanol 3:2 was applied to the HPTLC plate.

Standard 1A: 0.1% DGDG, (digalactosyldiacylglycerol) (Avanti, cat. #840524) dissolved in heptane:isopropanol 3:2 was applied in different amount (0.5-1-2-3 and 5 µL) to the HPTLC plate by an automatic TLC applicator.

Running buffer 4-1:Chloroform:Methanol:water 192:78:12 (standard running buffer for dough lipids)

Running buffer 6:Methylacetate:Chloroform:1-propanol:Methanol:0.25% KCl in water 25:25:25:10:9 (Used to better separation of Phospholipids)

10 mL running buffer in the plate chamber and 25 mL in the filter paper chamber

After development the TLC chromatogram was scanned and the area of the different component calculated using a CAMAG TLC scanner.

Based on the area of the DGDG standards a calibration curve was constructed and the concentration of the individual components of the flour lipids was calculated based on this calibration curve.

P-NMR Analysis:

Lecithin samples (40±5 mg) were dissolved in 1 mL 4:2:3 $CDCl_3$: MeOH: CsCDTA (aq) (deuterochloroform:methanol: caesium-1,2-diaminocyclohexanetetraacetic acid, v/v). The CDTA solution was prepared with a concentration of 1 M in milli-Q-water. $CsOH \cdot H_2O$ (Caesium hydroxide·water) was then added to adjust the pH to 10.5. The samples were vortexed for 10 s and centrifuged at 4500 rpm for 10 min at 20° C., then 550 µL was transferred to a 5 mm NMR tube using a 1000 µL Hamilton syringe and placed in the NMR instrument for analysis. Triisobutyrate phosphate was used as internal standard (2 mg). We found NMR spectra acquired at 5° C. yielded ideal spectra with optimum peak widths and signal dispersion.

NMR spectra were acquired under automation at 14.1 T using a Bruker Advance III spectrometer (Fällanden, Switzerland), a SampleJet sample changer (Bruker, Fällanden, Switzerland) and a 5 mm BBO (Broadband Observe) probe tuned to phosphorous (Bruker, Fällanden, Switzerland). Spectra were acquired under quantitative conditions.

LC/MS Analysis of Phospholipids Extracted from Dough:

The dough lipid samples were analyzed by liquid chromatography coupled on-line with a triple quadrupole mass spectrometer in full scan m/z 50-1500 with heated electro spray in positive and negative mode. NALPE formed deprotonated ions, [M-H]⁻ in negative mode.

The column was a normal phase column (DIOL) and the mobile phase was acetonitrile/acetone 80/20 with addition of 20 mL water in 1 L. The water contained 5 mM ammonium formate.

Samples were solved in 2 mL acetonitrile/acetone (80:20). The traces of selected NALPE were extracted and the areas were compared.

Instrumental

Agilent 1100

Binary pump (G1312B)+µ-Vacuum Degasser (G1379B)

High Performance autosampler ALS (G1367E)+Thermostat 1290 (G1330B)

Column compartment (G1316A)

TSQ Vantage, Triple quadrupole mass spectrometer from Thermo Finnigan with Heated-electrospray interface (HESI-II) (MS7)

Column: YMC Pack Diol 120 S-5 µm, 12 nm 4.6*50 mm (#526)

Chromatographic

| Autosampler temp: | 25° C. | Injection volume | 40 µL |
|---|---|---|---|
| Column temperature | 30° C. | | |

Sample Preparation

Lipid from 0.2 gram dry dough was added 2 mL acetonitrile/acetone (80:20) and sonicated 10 min.

Centrifuged for 3 min. at 16,000 g and the supernatant was injected as is.

Calculation: Based on HPLC/MS analysis the amount of NALPE components with different fatty acids were determined, and the relative content of C16:0 NALPE, C18:0 NALPE, C18:1 NALPE, C18:2 NALPE, C18:3 NALPE was calculated.

Extraction of Dough Lipids.

Sample of fully proofed dough was frozen immediately in liquid nitrogen. The dough was then frozen and freeze dried. The dry dough was the grounded and sieves. 1.0 g sample was scales into a 15 ml centrifuge tube with lid. 7.5 mL water saturated butanol (WSB) was added and mixed on a Vortex. The sample was placed in water bath at 90° C. for 10 minutes and then placed on a RotaMix (25 rpm) for 30 minutes. The sample was again placed in water bath at 90° C. again for 10 minutes and then placed on a RotaMix for 30 minutes. The sample was centrifuged at 2000 rcf for 10 minutes. 1.5 mL organic phase was taken out into a dram glass and evaporated to dryness under a steam of nitrogen and used for either further analysis.

Example 1

Baking Experiment Testing POWERBAKE® 4080 in Combination with LYSOMAX® Oil

In this experiment POWERBAKE® 4080 was tested in combination with LYSOMAX® Oil in a recipe for Hard Crust Rolls.

| Recipe | Bakers % |
|---|---|
| Wheat flour | 100 |
| Compressed yeast | 6 |
| Salt | 1.6 |
| Sugar | 1.6 |
| Water (400 BU-2%) | 57 |
| Fungal alpha amylase (16.2 FAU/g) | 11 |
| Other Enzymes | variable |

Kneading on a Diosna spiral mixer. Water uptake for flour according to analysis: 400 BU-2%

Procedure

Mix all ingredients in a bowl, 1 minute slow speed—add water and knead 2 minutes slow and 6.5 minutes fast speed. Dough temperature must be approximate 26° C. 1350 g dough is scaled and moulded round by hand. The dough is rested in a heating cabinet for 10 minutes at 30° C.

The dough is moulded into 30 dough balls on a "GLIMIK™ rounder"—settings according to table on machine.

The dough is proofed for 45 minutes at 34° C., 85% RH and baked for 13 minutes at 200° C./2 l steam+5 minutes damper open (MIWE oven prog. 1). After baking the rolls are cooled for 25 minutes at ambient temperature before weighing and measuring of volume.

Dough and bread characteristics are evaluated by a skilled person

| Evaluation | Evaluation method | Lowest score = 1 | Highest score = 10 |
|---|---|---|---|
| Dough | | | |
| Dough development after mixing | Extend dough with fingers | Dough cannot be stretched without breaking | Dough can be stretched obtaining papery thin dough without breakage |
| Stickiness after mixing | Cut a big slit in all dough, open the dough, touch the cut dough surface with fingers | Dry surface. The dough slips your fingers | The dough sticks to your fingers |
| Extensibility after resting | Extend dough with fingers | Dough cannot be stretched without breaking | Dough can be stretched obtaining papery thin dough without breakage |
| Stickiness after resting | Cut a big slit in all dough, open the dough, touch the cut dough surface with fingers | Dry surface. The dough slips your fingers | The dough sticks to your fingers |
| Crust | | | |
| Crispiness of crust | Fracture crust using several fingers | Leathery crust | Crisp crust |
| Crumb | | | |
| Crumb pore size | Visual evaluation of sliced bread, size of gas bubbles in crumb | Open crumb, big gas bubbles | Fine crumb, small gas bubbles |
| Crumb pore homogeneity | Visual evaluation of sliced bread, homogeneity of gas bubbles | Big variation in sizes of gas bubbles | Constant gas bubble size |
| Product shape | | | |
| Capping/Hole under the crust | Visual evaluation of vertical cut surface | A very large hole directly under the crust. | No separation between crust and crumb. |
| Oven spring/Energy | Visual evaluation amount of energy in the product | No energy | High level of energy |

The experimental set up and results from the baking evaluation are shown in Table 1.

TABLE 1

Baking results from bread baked with POWERBAKE ® 4080 and LYSOMAX ® Oil

| | Trial no. | | | | | | |
|---|---|---|---|---|---|---|---|
| | 1 | 2 | 3 | 4 | 5 | 6 | 7 |
| Enzymes: | | | | | | | |
| POWERBAKE ® 4080, ppm | 0 | 30 | 40 | 30 | 30 | 40 | 40 |
| LYSOMAX ® Oil, ppm | — | — | — | 100 | 250 | 100 | 250 |
| Baking results: | | | | | | | |
| Specific Bread Volume (ccm/g) | 5.78 | 6.90 | 7.25 | 7.52 | 7.45 | 7.65 | 7.63 |
| Dough evaluation | | | | | | | |
| Dough develop. after mixing | 6 | 4 | 5 | 7 | 8 | 9 | 7 |
| Stickiness after mixing | 6 | 5 | 6 | 7 | 6 | 7 | 7 |
| Extensibility after resting | 5 | 8 | 4 | 6 | 6 | 8 | 8 |
| Stickiness after resting | 6 | 5 | 6 | 6 | 6 | 6 | 5 |
| Crispiness of crust | 6 | 6 | 8 | 8 | 9 | 9 | na |
| Crumb | | | | | | | |
| Crumb pore size | 6 | 7 | 8 | 8 | 7 | 7 | na |
| Crumb pore homogeneity | 6 | 6 | 7 | 8 | 6 | 7 | na |
| Oven spring/Energy | 7 | 10 | 10 | 10 | 10 | 10 | na |
| Total Dough + bread score* | 44 | 51 | 50 | 54 | 54 | 57 | na |

*Total dough + bread score = the sum of the individual scores with the correction that stickiness score is added as (10 - actual score)

Ex 1: Total dough+bread score=6+(10-6)+5+(10-6)+6+6+6+7=44

Fully fermented dough was frozen, freeze dried and lipids in the dry dough were extracted with water saturated butanol and analysed by HPTLC.

The components form the HPTLC analysis were quantified based on a calibration curve for DGDG analysed on the same plate with results shown in Table 2.

TABLE 2

HPTLC analysis of dough lipid components digalactosyldiglyceride (DGDG), digalactosylmonoglyceride (DGMG), monogalactosylmonoglyceride (MGMG), N-acyl phosphatidylethanolamine (NAPE), N-acyl lysophosphatidylethanolamine (NALPE), N-acyl glycerophosphatidylelthanolamine (NAGPE).

| POWERBAKE® 4080 ppm | LYSOMAX® Oil ppm | DGDG % | DGMG % | MGMG % | NAPE % | NALPE % | NAGPE % |
|---|---|---|---|---|---|---|---|
| 0 | 0 | 0.297 | 0.015 | 0.016 | 0.066 | 0.047 | 0.010 |
| 30 | 0 | 0.178 | 0.036 | 0.051 | 0.027 | 0.083 | 0.018 |
| 40 | 0 | 0.194 | 0.048 | 0.067 | 0.021 | 0.106 | 0.022 |
| 30 | 100 | 0.190 | 0.042 | 0.066 | 0.000 | 0.093 | 0.028 |
| 30 | 250 | 0.183 | 0.045 | 0.066 | 0.000 | 0.074 | 0.034 |
| 40 | 100 | 0.189 | 0.048 | 0.072 | 0.000 | 0.090 | 0.030 |
| 40 | 250 | 0.181 | 0.050 | 0.074 | 0.000 | 0.074 | 0.036 |

The baking results in Table 1 illustrate a strong effect on bread volume of adding POWERBAKE® 4080 to the dough. Addition of LYSOMAX® Oil in combination with 30 ppm Powerbake however further increases the bread volume, and a clear synergistic effect is seen. The synergistic effect is also seen as improvement of dough and bread score. 100 ppm LYSOMAX® Oil gives the strongest synergistic effect, HPTLC analysis confirms that POWERBAKE® 4080 has strong activity on both monogalactosyldiglyceride (MGDG) and digalactosyldiglyceride (DGDG) during the formation of monogalactosylmonoglyceride (MGMG) and digalactosylmonoglyceride (DGMG). This enzyme also has strong activity on NAPE during the formation of NALPE. LYSOMAX® Oil also has activity on NAPE during the formation NALPE. Some activity of LYSOMAX® Oil is also seen on galactolipids in dough.

Without wishing to be bound by theory, the synergistic baking performance between POWERBAKE® 4080 and LYSOMAX® Oil is due to the fact that LYSOMAX® Oil is active on the sn2 position of NAPE whilst POWERBAKE® is active on the sn1 position in polar lipids (including MGDG and DGDG and phospholipases—including NAPE).

Example 2

Baking Experiment Testing LYSOMAX® Oil in Dosage 25 ppm to 200 ppm

In Example 1 it was shown that the optimal dosage of LYSOMAX® Oil was 100 ppm in combination with POWERBAKE® 4080. In order to further study the dosage response, LYSOMAX® Oil was tested in dosage from 25 ppm to 200 ppm in combination, with POWERBAKE® 4080. Results are shown in Table 3.

TABLE 3

| | Trial No. | | | | | | | |
|---|---|---|---|---|---|---|---|---|
| | 1 | 2 | 3 | 4 | 5 | 6 | 7 | 8 |
| Enzymes: | | | | | | | | |
| LYSOMAX® Oil, ppm | 0 | 0 | 25 | 50 | 75 | 100 | 150 | 200 |
| POWERBAKE® 4080, ppm | 0 | 30 | 30 | 30 | 30 | 30 | 30 | 30 |
| Baking results: | | | | | | | | |
| Specific Volume (ccm/g) | 6.54 | 7.51 | 7.49 | 7.48 | 8.26 | 8.32 | 8.17 | 8.05 |
| Dough score | | | | | | | | |
| Dough develop. after mixing | 7 | 6 | 7 | 7 | 6 | 7 | 7 | 7 |
| Stickiness after mixing | 7 | 6 | 6 | 7 | 5 | 6 | 6 | 6 |
| Extensibility after resting | 4 | 5 | 6 | 5 | 4 | 6 | 7 | 5 |
| Stickiness after resting | 5 | 6 | 6 | 6 | 5 | 5 | 5 | 5 |
| Crust score | | | | | | | | |
| Crispiness of crust | 4 | 8 | 8 | 7 | 9 | 10 | 8 | 9 |
| Crumb score | | | | | | | | |
| Crumb pore size | 4 | 7 | 7 | 7 | 7 | 8 | 8 | 8 |
| Crumb pore homogeneity | 4 | 6 | 7 | 7 | 7 | 8 | 7 | 7 |
| Capping | 7 | 10 | 10 | 10 | 10 | 10 | 10 | 10 |
| Oven spring/Energy | 9 | 9 | 9 | 9 | 9 | 9 | 9 | 9 |

The baking results confirm a synergistic effect of 30 ppm POWERBAKE® 4080 combined with LYSOMAX® Oil. A minimum of 75 ppm LYSOMAX® Oil is needed to see the synergistic effect and the optimum dosage in 100 ppm.

Fully fermented doughs were frozen, freeze dried and lipids in the dry dough were extracted with water saturated butanol and analysed by HPTLC (Table 4).

TABLE 4

HPTLC analysis of dough lipids.

| POWERBAKE® 4080 ppm | LYSOMAX® Oil ppm | DGDG % | MGMG % | NAPE % | NALPE % | NAGPE % |
|---|---|---|---|---|---|---|
| 0 | 0 | 0.293 | 0.016 | 0.087 | 0.053 | 0.012 |
| 30 | 0 | 0.204 | 0.062 | 0.019 | 0.101 | 0.021 |
| 30 | 25 | 0.210 | 0.059 | 0.018 | 0.091 | 0.022 |
| 30 | 50 | 0.198 | 0.063 | 0.000 | 0.092 | 0.023 |
| 30 | 75 | 0.201 | 0.068 | 0.000 | 0.088 | 0.025 |
| 30 | 100 | 0.184 | 0.063 | 0.000 | 0.075 | 0.027 |
| 30 | 150 | 0.186 | 0.061 | 0.000 | 0.073 | 0.028 |
| 30 | 200 | 0.193 | 0.062 | 0.000 | 0.066 | 0.030 |

The analysis of dough lipids confirms the activity of LYSOMAX® Oil on NAPE, but it is also seen that the amount of NALPE decreases with increased dosage of LYSOMAX® Oil and that NAGPE is formed. A dosage of 25 to 200 ppm LYSOMAX® Oil has very little effect on the galactolipids.

The dough lipids were also analysed by P-NMR with focus on the isomer composition of NALPE, shown in table 5. The results from table 5 indicate that more 1-NALPE is produced with increasing dosage of LYSOMAX® Oil because of the sn2 specificity of this enzyme.

TABLE 5

P-NMR analysis of phospholipids in dough lipids.

| LYSOMAX® Oil ppm | POWERBAKE® 4080 ppm | 1-NALPE Relative NMR response | 2-NALPE Relative NMR response | NAPE Relative NMR response | 1-NALPE/2-NALPE ratio |
|---|---|---|---|---|---|
| 0 | 0 | 742 | 191 | 1570 | 3.9 |
| 0 | 30 | 985 | 619 | 581 | 1.6 |
| 25 | 30 | 982 | 512 | 462 | 1.9 |
| 50 | 30 | 1011 | 500 | 333 | 2.0 |
| 75 | 30 | 975 | 504 | 297 | 1.9 |
| 100 | 30 | 878 | 422 | 261 | 2.1 |
| 150 | 30 | 926 | 448 | 356 | 2.1 |
| 200 | 30 | 818 | 323 | 148 | 2.5 |

Example 3

Baking Experiment Testing POWERBAKE® 4080 in Combination with MAXAPAL®

In this experiment POWERBAKE® 4080 was tested in combination with MAXAPAL® or LYSOMAX® Oil in Hard Crust Roll recipe.

MAXAPAL® is a phospholipase with high PLA2 specificity.

The experimental set up and baking results are shown in Table 6.

TABLE 6

Baking experiment with POWERBAKE® 4080, LYSOMAX® Oil and MAXAPAL® Enzyme dosing based on flour.

| | Trial No | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Enzymes: | | | | | | | | | | | | |
| POWERBAKE® 4080, ppm | . | 30 | . | 30 | 30 | 30 | 30 | 30 | 50 | 50 | 40 | 40 |
| MAXAPAL®, ppm | . | . | 500 | . | 100 | 250 | 500 | 750 | . | 500 | . | 500 |
| LYSOMAX® Oil, ppm | . | . | . | 100 | . | . | . | . | . | . | . | . |

TABLE 6-continued

Baking experiment with POWERBAKE ® 4080, LYSOMAX ® Oil and MAXAPAL ® Enzyme dosing based on flour.

| | Trial No | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Baking results: | | | | | | | | | | | | |
| Specific Volume (ccm/g) | 5.96 | 6.96 | 6.43 | 7.65 | 7.65 | 7.68 | 7.84 | 7.88 | 7.61 | 7.57 | 7.71 | 7.94 |
| Dough evaluation: | | | | | | | | | | | | |
| Dough develop. After mixing | 7 | 6 | 7 | 7 | 7 | 9 | 8 | 6 | 8 | 8 | 6 | 7 |
| Stickiness after mixing | 7 | 7 | 6 | 6 | 6 | 5 | 5 | 5 | 5 | 6 | 7 | 6 |
| Extensibility after resting | 4 | 6 | 5 | 4 | 4 | 5 | 4 | 5 | 6 | 8 | 6 | 5 |
| Stickiness after resting | 6 | 6 | 5 | 6 | 5 | 6 | 5 | 6 | 7 | 5 | 5 | 5 |
| Crust: | | | | | | | | | | | | |
| Crispiness of crust | 5 | 6 | 5 | 6 | 6 | 8 | 7 | 8 | 8 | 9 | 8 | 8 |
| Crumb: | | | | | | | | | | | | |
| Crumb pore size | 5 | 6 | 5 | 7 | 8 | 8 | 8 | 8 | 7 | 7 | 8 | 8 |
| Crumb pore homogeneity | 4 | 5 | 4 | 7 | 7 | 7 | 7 | 7 | 7 | 7 | 7 | 7 |
| Capping | 5 | 6 | 6 | 7 | 7 | 10 | 10 | 9 | 10 | 9 | 9 | 9 |
| Oven spring/Energy | 5 | 6 | 6 | 6 | 7 | 7 | 8 | 8 | 8 | 8 | 8 | 9 |
| Total dough + bread score: | 42 | 48 | 47 | 52 | 55 | 63 | 62 | 60 | 62 | 65 | 60 | 62 |

The total dough and bread score is calculated as the sum of the individual score apart from stickiness score, which is added as (10-stickiness)

Experiment 1:Total score=7+(10−7)+4+(10−6)+5+5+ 4+5+5=42

The results from Table 6 clearly illustrate that a combination of POWERBAKE® 4080 with Maxapal produces at clear synergistic effect with regard to bread volume and the dough and bread characteristics are also improved. It is also observed that MAXAPAL® is very tolerant to different dosages, where increased effect is seen from 100 to 750 ppm dosage of MAXAPAL®.

Fully fermented doughs were frozen, freeze dried and lipids in the dry dough were extracted with water saturated butanol and analysed by HPTLC.

The components form the HPTLC analysis were quantified based on a calibration curve for DGDG analysed on the same plate with results shown in Table 7.

is very specific for NAPE and no significant formation of NAGPE is observed. This might explain why Maxapal is tolerant to different dosage. MAXAPAL® has no activity on DGDG, but small activity on MGDG illustrated as MGMG formation was observed. Without wishing to be bound by theory, the specificity of MAXAPAL® with regard to hydrolysis of NAPE to NALPE explains why this enzyme has positive synergistic effect in combination with POWERBAKE® 4080 and this also explains why MAXAPAL® cannot easily be overdosed. It is however seen that combination of POWERBAKE® 4080 and MAXAPAL® produces small amount of NAGPE. This can be explained by the fact that MAXAPAL® produces sn1-NALPE which is a more preferred substrate for POWERBAKE® 4080 than sn2-NALPE, because POWERBAKE® 4080 is active on the fatty acid at the sn1 position.

In order to study in further detail the specificity of the enzymes and the impact on the fatty acid composition of

TABLE 7

HPTLC analysis of dough lipids.

| POWERBAKE ® 4080 ppm | MAXAPAL ® ppm | LYSOMAX ® Oil ppm | DGDG % | DGMG % | MGMG % | NAPE % | NALPE % | NAGPE % |
|---|---|---|---|---|---|---|---|---|
| . | . | . | 0.298 | 0.052 | 0.010 | 0.074 | 0.034 | 0.008 |
| 30 | . | . | 0.234 | 0.062 | 0.055 | 0.021 | 0.100 | 0.017 |
| . | 500 | . | 0.297 | 0.040 | 0.023 | 0.000 | 0.129 | 0.011 |
| 30 | . | 100 | 0.231 | 0.061 | 0.062 | 0.000 | 0.090 | 0.031 |
| 30 | 100 | . | 0.234 | 0.067 | 0.062 | 0.000 | 0.106 | 0.023 |
| 30 | 250 | . | 0.239 | 0.058 | 0.068 | 0.000 | 0.112 | 0.025 |
| 30 | 500 | . | 0.236 | 0.058 | 0.068 | 0.000 | 0.107 | 0.027 |
| 30 | 750 | . | 0.237 | 0.063 | 0.066 | 0.000 | 0.110 | 0.028 |
| 50 | . | . | 0.214 | 0.086 | 0.068 | 0.000 | 0.116 | 0.026 |
| 50 | 500 | . | 0.220 | 0.074 | 0.076 | 0.000 | 0.103 | 0.031 |
| 40 | . | . | 0.221 | 0.075 | 0.067 | 0.000 | 0.115 | 0.025 |
| 40 | 500 | . | 0.258 | 0.077 | 0.080 | 0.000 | 0.126 | 0.031 |

HPTLC analysis confirms that MAXAPAL® is very active on NAPE during formation of NALPE. The enzyme NALPE in dough the lipids extracted from the dough were analysed by HPLC/MS and the relative composition of NALPE with C16:0, C18:0, C18:1, C18:2 and C18:3 fatty acid composition was analysed. Based on the fatty acid composition of NALPE in dough and based on the amount of NALPE calculated form TLC analysis of the dough lipids the relative amount of C16:0_NALPE in the dough was calculated as shown in table in Table 8. (Relative amount of C16:0_NALPE in the control dough was defined to 100%.)

TABLE 8

Relative amount of C16:0 NALPE in enzyme treated dough.

| Baking test | POWERBAKE ® 4080 ppm | MAXAPAL ® ppm | LYSOMAX ® Oil ppm | Relative % NALPE_16:0 |
|---|---|---|---|---|
| 1 | — | — | — | 100 |
| 2 | 30 | — | — | 103 |
| 3 | — | 500 | — | 340 |
| 4 | 30 | — | 100 | 175 |
| 5 | 30 | 100 | — | 142 |
| 6 | 30 | 250 | — | 231 |
| 7 | 30 | 500 | — | 329 |
| 8 | 30 | 750 | — | 328 |
| 9 | 50 | — | — | 108 |
| 10 | 50 | 500 | — | 244 |
| 11 | 40 | — | — | 108 |
| 12 | 40 | 500 | — | 296 |

The results in Table 7 and Table 8 confirm that POWERBAKE® 4080 produces significant amount of NALPE in the dough, but the amount of C16:0_NALPE only increase marginal (3 to 8%). This is explained by the fact that POWERBAKE® 4080 hydrolyse the fatty acid at the sn1 position of NAPE. When dough is treated with MAXAPAL® the amount of NALPE in the dough also increases and here it is observed that the amount of C16:0_NALPE increases strongly (340%), because MAXAPAL® hydrolyse the fatty acid in the sn2 position of NAPE.

When POWERBAKE® 4080 is combined with MAXAPAL® it is possible to increase the amount of C16:0_NALPE, and as shown in Table 7 this enzyme combination is also active on galactolipids like DGDG and MGDG in the dough during production of DGMG and MGMG.

The positive synergistic effect of POWERBAKE® 4080 and MAXAPAL® on baking performance was explained by the combined effect on galactolipids and NAPE during formation of DGMG, MGMG and 16:0_NALPE. MAXAPAL® is also active on other phospholipids like PC and PE in the dough, and it is known that these components also have more saturated fatty acid at the sn1 position. It is therefore expected that LPC and LPE produced in the dough also has a higher amount of saturated (c16:0) fatty acid.

Example 4

Baking Experiment with Crusty Rolls

The purpose of this experiment was to test another PLA2, LIPOMOD™ 699L from Biocatalysts and investigate the effect in combination with a sn1 specific enzyme POWERBAKE® 4080.

The enzymes were tested according to the procedure for Hard Crust Rolls (Example 1) and specific bread volume and dough and bread properties were evaluated.

The enzymes were tested as outlined in table 9 and the baking results are also shown in Table 9.

TABLE 9

Baking experiment with POWERBAKE ® 4080 and LIPOMOD ™ 699L. Enzyme dosing based on flour weight.

|  | 1 | 2 | 3 | 4 |
|---|---|---|---|---|
| POWERBAKE ® 4080, ppm | 0 | 30 | 0 | 30 |
| LIPOMOD ™ 699L, ppm | 0 | 0 | 500 | 500 |
| Specific Volume (ccm/g) | 6.02 | 6.70 | 6.39 | 7.74 |
| Dough development after mixing | 6 | 6 | 7 | 8 |
| Stickiness after mixing | 5 | 7 | 5 | 6 |
| Extensibility after resting | 8 | 7 | 6 | 6 |
| Stickiness after resting | 6 | 7 | 6 | 7 |
| Crispiness of crust | 5 | 6 | 5 | 7 |
| Crumb pore size | 5 | 8 | 7 | 8 |
| Crumb pore homogeneity | 5 | 7 | 7 | 7 |
| Capping | 6 | 8 | 7 | 10 |
| Oven spring/Energy | 6 | 7 | 7 | 9 |
| Total score | 50 | 55 | 55 | 62 |

The results from table 9 clearly show a synergistic effect by combining the PLA2, LIPOMOD™ 699L with a sn1 specific glycolipase POWERBAKE® 4080. LIPOMOD™ 699L on its own increases the bread volume a little and POWERBAKE® 4080 also clearly increases the bread volume. Combination of the two enzymes however increases the bread volume more than the individual enzymes. Also, the total dough and bread scores are clearly improved by combining the two enzymes.

Example 5

Baking Experiment with Hard Crust Rolls

In earlier baking tests it was shown that PLA2 enzymes showed synergistic effect in combination with a sn1 specific enzyme POWERBAKE® 4080. This enzyme also has sn1 specific phospholipase activity. In this test other sn1 specific phospholipases were tested in combination with MAXAPAL®, PLA2 as shown in Table 10.

The enzymes were tested according to the procedure for Hard Crust Rolls (Example 1) with the only change that a new Reform flour (DK2015-00040) was used.

TABLE 10

Baking experiment with MAXAPAL ®, LIPOPAN ™,
and PANAMORE ®; Enzyme dosing based on flour.

|  | 1 | 2 | 3 | 4 | 5 | 6 |
|---|---|---|---|---|---|---|
| MAXAPAL ®, ppm | 500 | 0 | 0 | 500 | 0 | 500 |
| LIPOPAN ™, ppm | 0 | 0 | 25 | 25 | 0 | 0 |
| PANAMORE ®, ppm | 0 | 0 | 0 | 0 | 10 | 10 |
| Specific Volume (ccm/g) | 6.2 | 5.64 | 5.99 | 7.27 | 6.69 | 7.37 |
| Dough development after mixing | 8 | 6 | 8 | 8 | 7 | 9 |
| Stickiness after mixing | 5 | 5 | 6 | 6 | 6 | 6 |
| Extensibility after resting | 4 | 4 | 4 | 4 | 4 | 8 |
| Stickiness after resting | 6 | 4 | 6 | 7 | 5 | 8 |
| Crispiness of crust | 8 | 4 | 4 | 6 | 6 | 7 |
| Crumb pore size | 6 | 7 | 9 | 8 | 8 | 5 |
| Crumb pore homogeneity | 6 | 7 | 8 | 8 | 7 | 5 |
| Capping | 9 | 7 | 4 | 9 | 9 | 9 |
| Oven spring/Energy | 7 | 7 | 7 | 7 | 7 | 7 |
| Total score | 57 | 53 | 52 | 57 | 57 | 56 |

The baking results obtained by combination of MAXAPAL® with PANAMORE® and LIPOPAN F™ clearly showed a synergistic effect on bread volume.

Example 6

Baking Experiment with Hard Crust Rolls

Baking experiments have shown that a combination of a sn1 specific enzyme POWERBAKE® 4080 and sn2 specific enzyme MAXAPAL® has a positive synergistic effect on bread volume when used in baking. It is however known that the amount of phospholipids in flour is rather limited. The aim of this test was to investigate the effect of these enzymes when the dough was enriched with soya lecithin.

The baking experiment was conducted according to the procedure for Hard Crust Rolls (Example 1) with enzymes and lecithin as shown in Table 11.

TABLE 11

Baking test with lecithin combined with enzymes.
Enzyme dosage based on flour.

| Baking test no. | POWERBAKE ® 4080 ppm | MAXAPAL ® #4313 ppm | SOLEC ™ B-10, lecithin % | Bread volume (ccm/g) |
|---|---|---|---|---|
| 1 |  |  |  | 5.90 |
| 2 |  |  | 0.2 | 6.15 |
| 3 |  | 500 | 0.2 | 6.26 |
| 4 | 30 |  | 0.2 | 5.91 |
| 5 | 30 | 500 | 0.2 | 7.08 |
| 6 |  |  | 0.5 | 6.43 |
| 7 |  | 500 | 0.5 | 6.57 |
| 8 | 30 |  | 0.5 | 6.58 |
| 9 | 30 | 500 | 0.5 | 7.13 |

The effect on bread volume shown in table 11 clearly confirms a synergistic effect of POWERBAKE® 4080 and MAXAPAL® in dough containing 0.2% or 0.5% lecithin.

Example 7

Baking Experiment with Hard Crust Rolls

In this baking experiment the effect of MAXAPAL® PLA2 and glycolipase POWERBAKE® 4080 was tested in Hard Crust Rolls using American flour called Polar Bear (DK2015-00071). The baking experiment was conducted according to the procedure for Hard Crust Rolls (Example 1) apart from that no fungal alpha amylase was added. The experimental setup and results are shown in Table 12.

TABLE 12

Baking experiment with POWERBAKE ® 4080 and
MAXAPAL ® in Polar Bear flour. Enzyme dosage based on flour.

|  | 1 | 2 | 3 | 4 |
|---|---|---|---|---|
| POWERBAKE ® 4080, ppm | 0 | 0 | 20 | 20 |
| MAXAPAL ®, ppm | 0 | 500 | 0 | 500 |
| Specific Volume (ccm/g) | 5.15 | 5.53 | 5.80 | 6.39 |
| Dough development after mixing | 7 | 6 | 6 | 8 |
| Stickiness after mixing | 7 | 7 | 7 | 7 |
| Extensibility after resting | 3 | 5 | 6 | 7 |
| Stickiness after resting | 2 | 2 | 3 | 3 |
| Crispiness of crust | 5 | 5 | 6 | 9 |
| Crumb pore size | 3 | 3 | 6 | 6 |
| Crumb pore homogeneity | 1 | 1 | 6 | 6 |
| Capping | 3 | 4 | 7 | 9 |
| Oven spring/Energy | 2 | 2 | 5 | 8 |
| Total | 35 | 37 | 52 | 63 |

The baking results from table 12 confirm the synergistic effect by combination of MAXAPAL® PLA2 and a glycolipase POWERBAKE® when these enzymes were tested in an American flour.

Example 8

Baking Experiment with Sponge and Dough Bread

Baking experiments have shown that it is possible to obtain a positive synergistic effect of sn1 and sn2 phospholipases with activity on NAPE in dough. The positive effect may be explained by the production of NALPE with saturated fatty acid (C16:0_NALPE) at the glycerol moiety. When added to a dough, these two types of enzymes will however compete for the NAPE substrate and it has therefore been observed that combination of the two enzymes produces less C16:0_NALPE than what is produced when sn2 specific phospholipase (MAXAPAL®) is used alone.

In certain bread making procedures like the Sponge and Dough procedure it is however possible to add enzymes both on the sponge and on the dough side. When the sn2 specific phospholipase is added on the sponge side alone there will be no competition for the NAPE substrate. It is envisaged herein that a sn1 specific glycolipase may be added at the dough side.

Another aspect of adding the enzyme at the sponge side is that the functional polar components formed during sponge fermentation is available during dough mixing.

According to L. Gents et al. (Food Chemistry 172 (2015) 613-621), addition of emulsifiers like DATEM to the dough had impact on dough rheology, whereas the addition of lipase did not, because the hydrolysed lipids were released only to a significant level during fermentation. Addition of enzyme to the sponge in the Sponge and Dough bread making procedure forms hydrolysed lipids which have positive functional rheological properties on the dough.

In the following baking test MAXAPAL® was added to the sponge and POWERBAKE® 4080 was added at the dough side. The baking experiment was conducted according to the Sponge and Dough procedure taught below using Reform flour (DK2015-00040):

| Recipe | | | |
|---|---|---|---|
| | | | Bakers % |
| Sponge | Flour | % | 70 |
| | Water | % | 41.3 |
| | Compressed yeast | % | 3 |
| | Enzyme | | optional |
| Dough | Flour | % | 30 |
| | Salt | % | 1.5 |
| | Compressed yeast | % | 0.9 |
| | Sugar | % | 8 |
| | Ascorbic acid | ppm | 50 |
| | Rapeseed Oil | % | 2 |
| | Enzymes | ppm | optional |

Sponge:
1) Mix all ingredients 1 min 1st speed—3 min 2nd speed on Hobart Mixer
2) Sponge temp. must be app. 25.5° C.
3) Ferment sponge 3 hours at 30° C., 85% RH—unlidded bowl Dough:
1) Mix sponge and all remaining ingredients EXCEPT SALT for 2 min low—5 min medium on Hobart Mixer (use ice water)
2) Add salt—mix 8 min medium speed
3) Scale 550 g dough
4) Rest dough 10 min at ambient temperature
5) Mould on Glimek Molder: 1:4—2:3—3:15—4:12— width: 8 on both sides
6) Place moulded dough into tins
7) Proof 60 min at 43° C., 95% RH
8) Bake 26 min. at 200° C. (Miwe oven, prog 4)
9) Take breads out of tins and cool for 70 min. before weighing and measuring of volume The enzyme dosage and baking results are shown in Table 13.

TABLE 13

Baking experiment with POWERBAKE ® 4080 and MAXAPAL ® in Sponge and Dough procedure. Enzyme dosage based on flour.

| Baking test no. | MAXAPAL ® ppm to sponge | POWERBAKE ® 4080 ppm to dough | Specific Volume (ccm/g) Average |
|---|---|---|---|
| 1 | 0 | 0 | 5.78 |
| 2 | 250 | 0 | 5.81 |
| 3 | 0 | 10 | 5.83 |
| 4 | 250 | 10 | 6.07 |

The results in table 13 confirm that it is possible to obtain positive synergistic effect of MAXAPAL® and POWERBAKE® 4080 in a Sponge and Dough bread procedure where MAXAPAL® is added to the sponge and POWERBAKE® is added to the dough.

Example 9

Baking Experiment with Sponge and Dough Bread

Sponge and Dough bread making procedure has traditionally been used and is still widely used in the US baking industry. The Sponge and Dough procedure is characterized by two step dough mixing. The sponge is made by mixing flour (70% of total flour), water and yeast, which is fermented for quite a long time (3 hr). The sponge is then mixed with the remaining flour, water, sugar, salt and other ingredients. Normally enzymes are also added to the dough, but in the case of adding two enzymes which will compete for the same substrate, it is possible to add one enzyme at the sponge side, and then add the other enzymes at the dough side.

In the following experiment MAXAPAL® and POWERBAKE® 4080 were tested in a Sponge and Dough bread making procedure using an American flour (Polar Bear #DK2015-00071) the enzymes were tested with results as shown in Table 14.

TABLE 14

Baking experiment with POWERBAKE ® 4080 and MAXAPAL ® in Sponge and Dough procedure using Polar Bear flour. Enzyme dosage based on flour.

| Baking test no. | MAXAPAL ® ppm added to sponge | POWERBAKE ® 4080 ppm added to the dough | Specific Volume (ccm/g) |
|---|---|---|---|
| 1 | 0 | 0 | 5.28 |
| 2 | 250 | 0 | 5.27 |
| 3 | 0 | 10 | 5.61 |
| 4 | 250 | 10 | 6.02 |

The results from table 14 confirm a synergistic effect on bread volume when MAXAPAL® added to the sponge is combined with POWERBAKE® 4080 added to the dough.

Example 10

Baking Experiment with Sponge and Dough

The effect of addition of MAXAPAL® in combination with POWERBAKE® 4080, was further investigated in Sponge and Dough bread procedure with MAXAPAL® added either to the sponge or to the dough side. The experimental setup and results are shown in Table 15.

TABLE 15

Baking experiment with POWERBAKE ® 4080 and MAXAPAL ® in Sponge and Dough procedure using Polar Bear flour. Enzyme dosage is based on flour.

| MAXAPAL ® ppm, added to dough | MAXAPAL ® ppm, added to sponge | POWERBAKE ® 4080 ppm, added to dough | Sp. Bread volume ccm/g |
|---|---|---|---|
| 0 | 0 | 0 | 5.67 |
| 0 | 250 | 0 | 5.93 |
| 0 | 0 | 10 | 5.64 |
| 0 | 250 | 10 | 6.33 |
| 250 | 0 | 0 | 6.03 |
| 250 | 0 | 10 | 6.28 |

The bread volume results in table 15 confirm that a positive synergistic effect was obtained by adding a combination of MAXAPAL® and POWERBAKE® 4080. The synergistic effect is observed for addition of MAXAPAL® to both the sponge and to the dough side. The results indicate a stronger synergistic effect when MAXAPAL® was added to the sponge side.

Example 11

Baking Experiment Testing Softness Observed in White Pan Bread (Sponge & Dough) Using a Phospholipase A2 Enzyme which Acts on N-Acyl Phosphatidyl Ethanolamine at the Sn2 Position in Combination with an Enzyme that Acts on a Polar Lipid at the Sn1 Position The effect of addition of a phospholipase A2 enzyme which acts on N-acyl phosphatidyl ethanolamine at the sn2 position (MAXAPAL®) in combination with an enzyme that acts on a polar lipid at the sn1 position (POWERBAKE® 4090) was further investigated in White Pan Bread (Sponge and Dough bread procedure) with MAXAPAL® being added at the sponge stage and POWERBAKE® 4090 being added at the dough stage.

POWERBAKE® 4090 is an enzyme that acts on a polar lipid at the sn1 position. In particular, it is a fungal lipolytic enzyme having PLA1 activity on polar lipids and having SEQ ID NO: 1 disclosed herein. POWERBAKE® 4090 with an enzyme activity of 15,500 TIPU was used.

| Test | Description |
|---|---|
| 1 | Control |
| 2 | MAXAPAL ®. 250 ppm |
| 3 | POWERBAKE ® 4090. 3.23 ppm |
| 4 | MAXAPAL ®/POWERBAKE ® 4090. 250 ppm/3.23 ppm |

Usage of SUREBAKE® 800 (HOX) and ascorbic acid was kept constant at respectively 50 and 60 ppm for all experiments.

Two loaves from each test variable were tested and the softness (or hardness) of bread slices was determined from a texture profile analysis (TPA) using a Texture analyser TAXTplus from Stable Microsystems. A 35 mm metal probe on days 1 and 3 was used.

Figure 2:
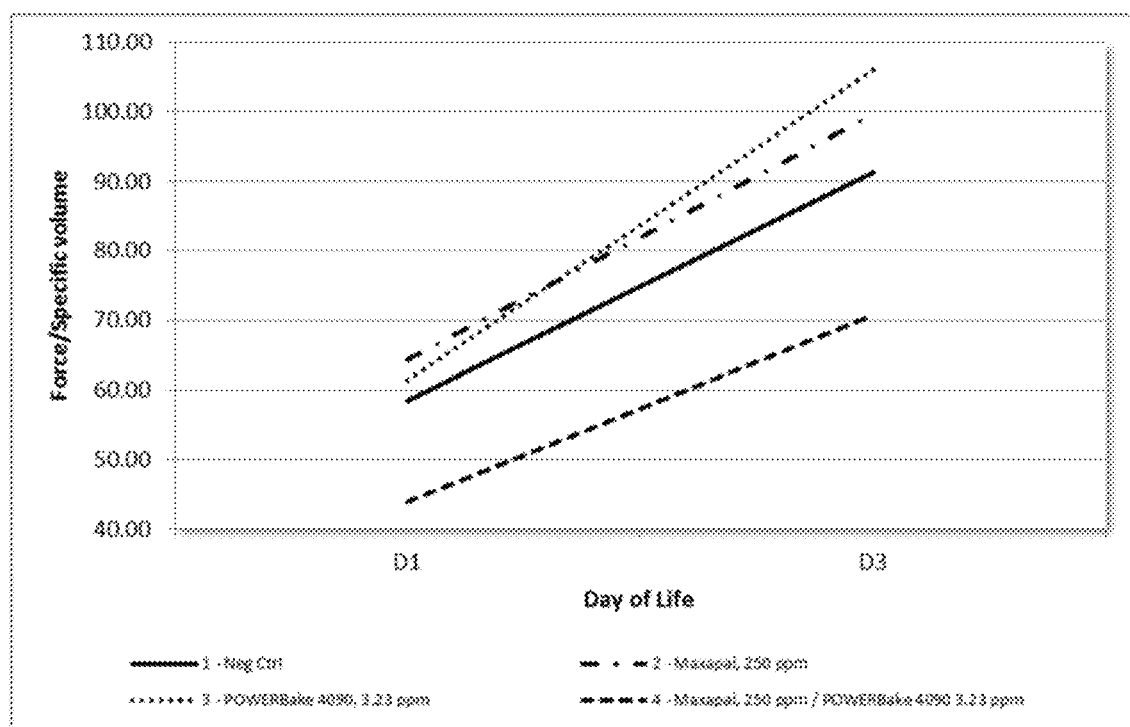
FIG. 2 shows the softness effect observed when a phospholipase A2 enzyme (SEQ ID NO: 3) which acts on N-acyl phosphatidyl ethanolamine at the sn2 position (MAXAPAL®); and an enzyme that acts on a polar lipid at the sn1 position (POWERBAKE® 4090) in combination is used in baking white pan bread.

Softness Results:

Testing respectively MAXAPAL® and POWERBAKE® 4090 separately showed need for higher force compared to control (no MAXAPAL® or POWERBAKE® 4090 added) indicating harder bread. Combining MAXAPAL® and POWERBAKE® 4090 provided the best softness. Same combination also showed the highest synergy in respect to volume (data not presented here). The bread softness results, as shown in FIG. 2, confirm that a positive synergistic effect is obtained by adding a combination of MAXAPAL® and POWERBAKE® 4090. This synergistic effect was observed in the production of white pan bread.

Example 12

Baking Experiment Testing Softness Observed in 100% Whole Wheat Bread (Sponge & Dough) Using a Phospholipase A2 Enzyme which Acts on N-Acyl Phosphatidyl Ethanolamine at the Sn2 Position in Combination with an Enzyme that Acts on a Polar Lipid at the Sn1 Position The effect of addition of a phospholipase A2 enzyme which acts on N-acyl phosphatidyl ethanolamine at the sn2 position (MAXAPAL®) in combination with an enzyme that acts on a polar lipid at the sn1 position POWERBAKE® 4090 was further investigated in 100% Whole wheat (Sponge and Dough) bread procedure with MAXAPAL® being added at the sponge stage and POWERBAKE® 4090 being added at the dough stage.

| Test | Description |
|---|---|
| 1 | Control |
| 2 | MAXAPAL ®. 250 ppm |
| 3 | POWERBAKE ® 4090. 3.23 ppm |
| 4 | MAXAPAL ®/POWERBAKE ® 4090. 250 ppm/3.23 ppm |

Usage of SUREBAKE® 800 (HOX) and ascorbic acid was kept constant at respectively 100 and 100 ppm for all experiments Two loaves from each test variable were tested and the softness (or hardness) of bread slices was determined from a texture profile analysis (TPA) using a Texture analyser TAXTplus from Stable Microsystems. A 35 mm metal probe on days 1 and 3 was used.

Softness Results:

PLA2 alone showed increased softness compared to the control (no MAXAPAL® or POWERBAKE® 4090 added) at both day 1 and day 3.

POWERBAKE®4090 showed softness on level (or lower) than control (no Maxapal® or POWERBAKE® 4090 added).

Combining MAXAPAL® and POWERBAKE® 4090 showed increased softness.

Figure 3:
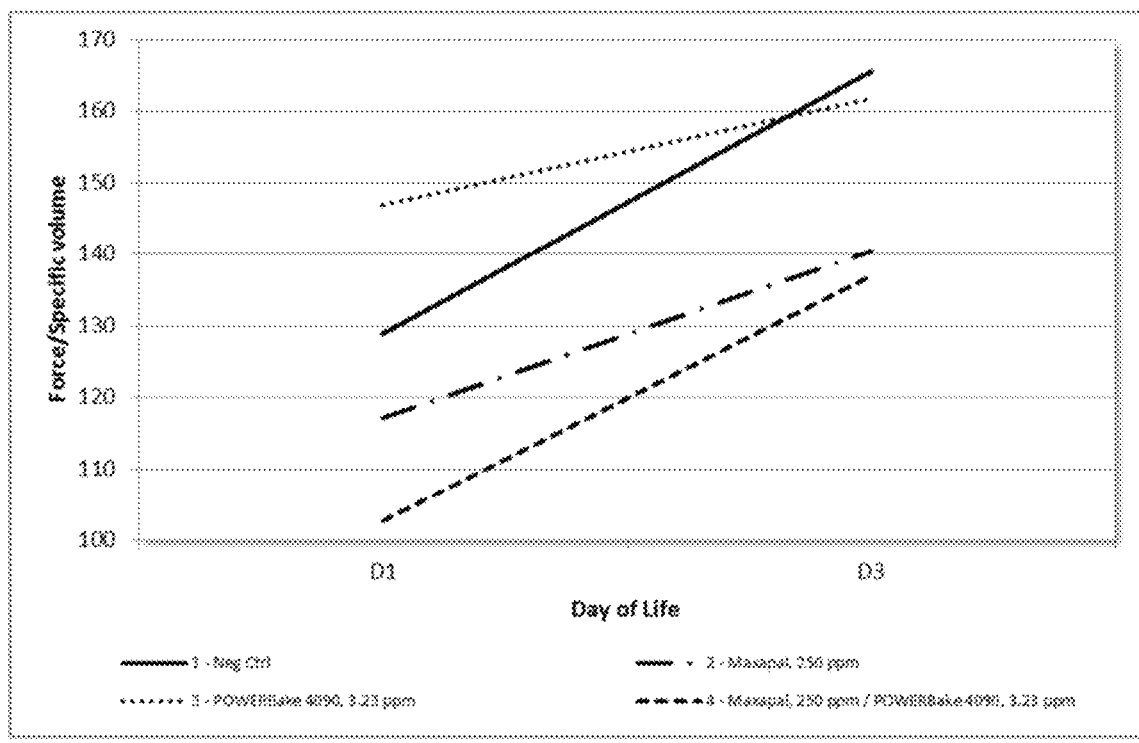
FIG. 3 shows the softness effect observed when a phospholipase A2 enzyme which acts on N-acyl phosphatidyl ethanolamine at the sn2 position (MAXAPAL®); and an enzyme that acts on a polar lipid at the sn1 position (POWERBAKE® 4090) in combination is used in baking 100% whole wheat bread.

The bread softness results, as shown in FIG. 3, in 100% whole wheat show that MAXAPAL® alone increases softness compared to the control (no MAXAPAL® or POWERBAKE® 4090 added). However, combining MAXAPAL® with POWERBAKE® 4090 further increases the softness compared to MAXAPAL® alone or POWERBAKE® 4090 alone or the control.

Example 13

Characteristics and Baking Performance of a Sn2 Specific, NAPE Active PLA2

The purpose of these experiments was to verify the synergistic performance in baking application for another phospholipase (CRC08335) with sn2 specificity and NAPE activity when combined with the sn1 specific enzyme POWERBAKE® 4080.

Method:

Gaschromatography (GLC)

Free fatty acid was analysed by GLC as trimethyl silyl derivatives (TMS).

Apparatus

Perkin Elmer *Clarus* 600 Capillary Gas Chromatograph equipped with WCOT fused silica column 12.5 m×0.25 mm ID×0.1µ film thickness 5% phenyl-methyl-silicone (CP Sil 8 CB from Chrompack).

Carrier gas: Helium.

Injector: PSSI cold split injection (initial temp 90° C. heated to 395° C.), volume 1.0 µl Detector FID: 395° C.

| | Oven program: | | | |
|---|---|---|---|---|
| | 1 | 2 | 3 | 4 |
| Oven temperature, ° C. | 80 | 200 | 240 | 360 |
| Isothermal, time, min. | 2 | 0 | 0 | 10 |
| Temperature rate, ° C./min. | 20 | 10 | 12 | |

Sample Preparation:

Evaporated sample is dissolved in 1.5 ml Heptane:Pyridin, 2:1. 500 µl sample solution is transferred to a crimp vial, 100 µl MSTFA (N-Methyl-N-trimethylsilyl-trifluoraceamid) is added and reacted for 15 minutes at 60° C.

Cloning of CRC08335

A synthetic gene (CRC08335) encoding a fungal phospholipase A2 type-2 was ordered from Generay (http://www.generay.com.cn/english/) as a codon-optimized gene for expression in Trichoderma reesei. The protein sequence of CRC08335 (SEQ ID NO. 4) (FIG. 5) was identified from an internal Myceliophthora thermophile strain and shares 95% identity with its closest homolog in the NCBI database (a secretory phospholipase A2 from Thermothelomyces thermophila ATCC 42464 with the NCBI accession number XP_003666499.1). CRC08335 has an N-terminal signal peptide sequence per prediction by SignalP 4.0 (SignalP 4.0: discriminating signal peptides from transmembrane regions. Thomas Nordahl Petersen, Soren Brunak, Gunnar von Heijne & Henrik Nielsen. Nature Methods, 8:785-786, 2011), suggesting that it is an extracellular enzyme.

Figure 7:
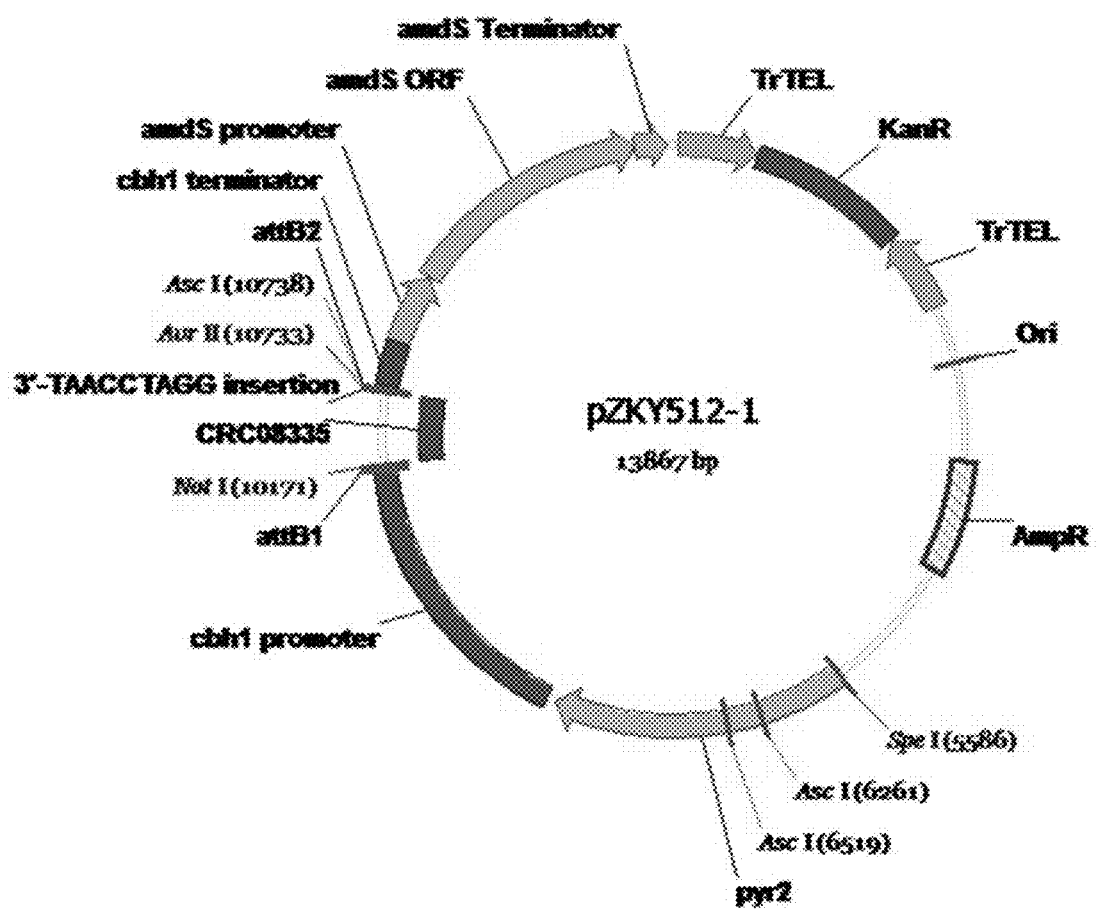
FIG. 7 shows the Plasmid map of pZKY512-1 harboring the synthetic gene of CRC08335.

The synthetic gene of CRC08335 (SEQ ID NO. 5) (FIG. 6), which retains its N-terminal native signal peptide, was cloned into pGXT (the same as the pTTTpyr2 vector described in published PCT Application WO2015/017256, incorporated by reference herein). In the pTTTpyr2 vector, the Aspergillus nidulans pyrG gene is replaced with the H. jecorina pyr2 gene. The pTTT-pyr2 expression vector contained the Trichoderma reesei cbhl-derived promoter (cbhl) and cbhl terminator regions allowing for a strong inducible expression of the gene of interest. The A. nidulans amdS and pyr2 selective markers confer growth of transformants on acetamide as a sole nitrogen source, and the Trichoderma reesei telomere regions allow for non-chromosomal plasmid maintenance in a fungal cell. After cloning of CRC08335, the resultant plasmid was labelled pZKY512-1. A plasmid of pZKY512-1 is provided in FIG. 7.

The protein sequence of CRC08335 identified from an internal Myceliophthora thermophile strain is set forth as SEQ ID NO. 4. The polypeptide sequence of the predicted signal peptide is MKFLSTALCLASSVLA (SEQ ID NO: 6).

Transformation of CRC08335

The plasmid pZKY512-1 was transformed into a suitable Trichoderma reesei strain (method described in published PCT application WO 05/001036) using protoplast transformation (Te'o et al. (2002) J. Microbiol. Methods 51:393-99). Transformants were selected on a solid medium containing acetamide as the sole source of nitrogen. After 5 days of growth on acetamide plates, transformants were collected and subjected to fermentation in 250 mL shake flasks in defined media containing a mixture of glucose and sophorose.

Results

SN1/SN2 SPECIFICITY:

Enzyme specificity for CRC08335 was determined according to 'Assay for the Determination of phospholipase activity and sn1 and sn2 position specificity on PC (phosphatidylcholine)'. The assay use PC substrate with a tailored FFA (free fatty acid) composition analysing the liberated FFA by GLC analysis. Results are outlined in table 16.

TABLE 16

Enzyme sn1/sn2 specificity of POWERBake ® 4080, MAXAPAL ® and CRC08335.

| | % Relative PLA1 Activity | % Relative PLA2 Activity |
|---|---|---|
| POWERBake ® 4080 (KLM1) | 82 | 18 |
| MAXAPAL ® | 5 | 95 |
| CRC08335 | 17 | 83 |

Data in table 16 clearly show that MAXAPAL® and CRC08335 to be sn2 specific as indicated by the high '% Relative PLA2 Activity' compared to '% Relative PLA1 Activity'. Also, data clearly reflects the POWERBake® 4080 as being sn1 specific.

Nape Activity:

NAPE activity of CRC08335 was evaluated by lipid profile analysis of dough from baking trials conducted with and without enzyme addition. Baking application was conducted according to the procedure for Hard Crust Rolls (Example 1).

NAPE activity was verified by HPLC analysis of dough lipid. Dough lipids were extracted from fully proofed, freeze dried doughs according to procedure for extraction of lipids form dough. The isolated lipids were analysed by HPLC using a HILIC DIOL column 1.7 µm, 50*2.1 mm (Fortis Technologies Ltd, UK). The solvents used were solvent A: 96% Acetone, 4% Methanol, 1 mM Ammonium formate and solvent B:60% Acetone, 34% Methanol, 6% MiliQ water, 1 mM Ammonium formate with the following gradient: 0-20 minutes 100% solvent A to 100% solvent B. 20-30 minutes 100% solvent B, 30-40 minutes 100% solvent A. NAPE and NALPE were quantified using a charged aerosol detector and 1-palmitoyl-sn-glycero-3-phosphoethanolamine-N-linoeoyl (Avanti Polar Lipids, Alabama, USA) as internal standard. The results from the HPLC analysis are shown in table 17.

TABLE 17

Baking experiment DK22102-43 testing POWERBake ® 4080 and CRC08335 in Hard Crust Rolls (Enzyme dosing based on flour weight; Reform flour)

| | | | Phospholipid component as measured by HPLC Result in % based on flour | |
|---|---|---|---|---|
| No | Treatment | Dosing | NAPE | NALPE |
| 1 | Negative control | No enzyme added | 0.14 | 0.07 |
| 2 | POWERBake ® 4080 | 30 ppm | 0.07 | 0.13 |
| 3 | CRC08335 | 1900 TIPU/kg flour | 0.09 | 0.12 |

The results in table 17 clearly show CRC08335 to have NAPE activity as shown by NAPE hydrolysis and generation of the more emulsifying component NALPE. POWERBake® 4080 also show NAPE activity as shown by NAPE hydrolysis and generation of the more emulsifying component NALPE. In addition to NALPE generation POWERBake® 4080 also show NAGPE generation (data not shown).

Application Performance:

The synergistic application performance of the sn2 specific, NAPE active enzyme CRC08335 when combined with POWERBake® 4080 was evaluated by baking trials conducted with and without enzyme addition. Baking application was conducted according to the procedure for Hard Crust Rolls (Example 1).

Synergistic application performance of CRC08335 and POWERBake® 4080 was shown by increased relative specific volume as outlined in table 18.

TABLE 18

Baking experiment DK22102-43 and DK22102-52 testing baking application performance of the Sn2 specific, NAPE active enzyme CRC08335 in combination with the sn1 specific POWERBake ® 4080.

| Baking trial | Treatment | Dosing | Specific volume relative to respective negative control |
|---|---|---|---|
| DK22102-43 | Negative control | — | 1 |
| | POWERBake ® 4080 | 30 ppm | 1.10 |
| | CRC08335 | 1900 TIPU/ kg flour | 1.06 |
| DK22102-52 | Negative control | — | 1 |
| | POWERBake ® 4080 | 30 ppm | 1.06 |
| | CRC08335/ POWERBake ® 4080 | 1900 TIPU/ kg flour/ 30 ppm | 1.23 |

Relative specific volume=Specific volume (Enzyme test)
a. Specific volume (Negative control)

The results in table 18 show that when used as single component the sn2 specific, NAPE active enzyme, CRC08335 has limited effect on specific volume. The combination of CRC08335 with POWERBake® 4080 (in respective dosage) and thus generation of emulsifying components from both phospho- and galacto-lipid hydrolyses show a clear synergistic effect upon specific volume.

CONCLUSION

Based on baking experiments and analysis of dough lipids it has surprisingly been found that combination of POWERBAKE® 4080 or POWERBAKE® 4090 with a MAXAPAL® PLA2 phospholipase or LYSOMAX® Oil, gives a positive synergistic effect in baking. This is confirmed by improvement of bread volume as well as improvement of dough and bread characteristics, including softness.

Positive synergistic effect on bread volume was also observed when MAXAPAL® was combined with other PLA1 enzymes like LIPOPAN F™ and PANAMORE®.

Baking tests with other PLA2 enzymes, LIPOMOD™ 699L and CRC08335 also showed positive synergistic effect in combination with POWERBAKE® 4080.

The synergistic effect was confirmed in different baking experiments using different types of wheat flour.

POWERBAKE® 4080 and POWERBAKE® 4090 is a glycolipase with sn1 activity on both galactolipids and phospholipids in dough. The PLA2 phospholipase, MAXAPAL® hydrolyse NAPE (and other phospholipids) at sn2 position during production of sn1-NALPE but does not to any significant degree hydrolyse NALPE. NAPE has different fatty acid composition at the sn1 and the sn2 position with typically more saturated fatty acids (C16:0 and C18:0) at the sn1 position. By HPLC/MS analysis it was shown that Maxapal contributed to a strong increase in C16:0_NALPE in dough.

Without being bound to the theory, it is expected that C16:0_NALPE has a stronger improvement on dough stability than C18:2 NALPE, because NALPE in aquatics system forms different mesomorphic phases depending on the fatty acid composition.

MAXAPAL® on its own did however not contribute with much effect on bread volume, but when it was combined with either POWERBAKE® 4080 or POWERBAKE® 4090 a strong synergistic effect is formed. This can be explained by the reaction products C16:0_NALPE, MGMG and DGMG produced by a combination of the two enzymes.

In some systems, MAXAPAL® and POWERBAKE® 4080 (or MAXAPAL® and POWERBAKE® 4090) when used in combination may compete for the NAPE substrate. This can be mitigated in certain bread making procedures where the dough is mixed in two steps, e.g. in the so called Sponge and Dough procedure. In this type of bread making it is possible to add MAXAPAL® (or other PLA2 with activity on NAPE) at the sponge side for optimal production of C16:0_NALPE and then add POWERBAKE® 4080 or POWERBAKE® 4090 at the dough side for production of DGMG and MGMG. A further advantage of adding MAXAPAL® at the sponge side was that the reaction products (e.g. NALPE) were readily available during dough mixing which contributes to improved dough properties.

The invention claimed is:

1. A method of making a dough, said method comprising admixing a dough component comprising flour, water or yeast, a phospholipase A2 enzyme which acts on N-acyl phosphatidyl ethanolamine at the sn2 position, said phospholipase A2 enzyme comprising SEQ ID NO:4, and an enzyme that acts on a polar lipid at the sn1 position, said enzyme comprising SEQ ID NO:1, wherein the phospholipase A2 enzyme and the enzyme that acts on a polar lipid at the sn1 position are admixed to the dough component in effective amounts that result in an increase of the specific volume of a baked product or steamed product or a boiled product or a fried product produced from the dough that is at least 10%, relative to a baked product or steamed product or boiled product or fried product made under identical conditions except for the addition of the phospholipase A2 enzyme and the enzyme that acts on a polar lipid at the sn1 position, wherein the phospholipase A2 enzyme is present at a concentration of between 150-2000 ePLU/kg flour and wherein the enzyme that acts on a polar lipid at the sn1 position is at 30 ppm.

2. The method of claim 1 wherein the method further comprises adding soya-based lecithin.

3. The method of claim 2, wherein the lecithin is enzymatically modified lecithin.

4. The method of claim 2, wherein the lecithin is enzymatically modified by an enzyme with phospholipase A2 activity.

5. The method of claim 4, wherein the method further comprises cooking the dough to produce a product.

6. The method of claim 5, wherein the dough is a dough selected from the group consisting of bread dough, pasta dough, noodle dough, cake dough, pastry dough or batter.

7. The method of claim 1, wherein a further enzyme is added to the dough.

8. The method of claim 7, wherein the further enzyme is one or more of: a lipase, starch degrading enzyme, a hemicellulase, a cellulase, an oxidoreductase, a lipid acyltransferase, a debranching enzyme, a lactase and a protease.

9. The method of claim 8, wherein the phospholipase A2 enzyme is added to a sponge and the enzyme that acts on a polar lipid at the sn1 position is added to the dough in a sponge-and-dough method.

* * * * *

SEQUENCE LISTING

```
<160> NUMBER OF SEQ ID NOS: 6

<210> SEQ ID NO 1
<211> LENGTH: 279
<212> TYPE: PRT
<213> ORGANISM: Fusarium heterosporum
<220> FEATURE:
<221> NAME/KEY: MISC_FEATURE
<223> OTHER INFORMATION: Phospholipase sn1;enzyme in POWERBAKE 4080 and
      POWERBAKE 4090 that acts on a polar lipid at the sn1 position
      (same as SEQ ID NO: 6 from US Patent 8,012,732; hereby
      incorporated by reference). This enzyme is known to have both
      gala

<400> SEQUENCE: 1

Glu Ala Glu Ala Ala Val Gly Val Thr Ser Thr Asp Phe Thr Asn Phe
1               5                   10                  15

Lys Phe Tyr Ile Gln His Gly Ala Ala Ala Tyr Cys Asn Ser Gly Thr
            20                  25                  30

Ala Ala Gly Ala Lys Ile Thr Cys Ser Asn Asn Gly Cys Pro Thr Ile
```

```
                35                  40                  45
Glu Ser Asn Gly Val Thr Val Ala Ser Phe Thr Gly Ser Lys Thr
 50                  55                  60
Gly Ile Gly Gly Tyr Val Ser Thr Asp Ser Ser Arg Lys Glu Ile Val
 65                  70                  75                  80
Val Ala Ile Arg Gly Ser Ser Asn Ile Arg Asn Trp Leu Thr Asn Leu
                 85                  90                  95
Asp Phe Asp Gln Ser Asp Cys Ser Leu Val Ser Gly Cys Gly Val His
                100                 105                 110
Ser Gly Phe Gln Asn Ala Trp Ala Glu Ile Ser Ala Gln Ala Ser Ala
                115                 120                 125
Ala Val Ala Lys Ala Arg Lys Ala Asn Pro Ser Phe Lys Val Val Ala
            130                 135                 140
Thr Gly His Ser Leu Gly Gly Ala Val Ala Thr Leu Ser Ala Ala Asn
145                 150                 155                 160
Leu Arg Ala Ala Gly Thr Pro Val Asp Ile Tyr Thr Tyr Gly Ala Pro
                165                 170                 175
Arg Val Gly Asn Ala Ala Leu Ser Ala Phe Ile Ser Asn Gln Ala Gly
            180                 185                 190
Gly Glu Phe Arg Val Thr His Asp Lys Asp Pro Val Pro Arg Leu Pro
        195                 200                 205
Pro Leu Ile Phe Gly Tyr Arg His Thr Thr Pro Glu Tyr Trp Leu Ser
210                 215                 220
Gly Gly Gly Gly Asp Lys Val Asp Tyr Ala Ile Ser Asp Val Lys Val
225                 230                 235                 240
Cys Glu Gly Ala Ala Asn Leu Met Cys Asn Gly Gly Thr Leu Gly Leu
                245                 250                 255
Asp Ile Asp Ala His Leu His Tyr Phe Gln Ala Thr Asp Ala Cys Asn
            260                 265                 270
Ala Gly Gly Phe Ser Trp Arg
        275

<210> SEQ ID NO 2
<211> LENGTH: 318
<212> TYPE: PRT
<213> ORGANISM: Aeromonas salmonicida
<220> FEATURE:
<221> NAME/KEY: MISC_FEATURE
<223> OTHER INFORMATION: mature lipid acyltransferase (GCAT) derived
      from Aeromonas salmonicida (See US patent 9,175,271)

<400> SEQUENCE: 2

Ala Asp Thr Arg Pro Ala Phe Ser Arg Ile Val Met Phe Gly Asp Ser
1               5                  10                  15
Leu Ser Asp Thr Gly Lys Met Tyr Ser Lys Met Arg Gly Tyr Leu Pro
                20                  25                  30
Ser Ser Pro Pro Tyr Tyr Glu Gly Arg Phe Ser Asn Gly Pro Val Trp
            35                  40                  45
Leu Glu Gln Leu Thr Lys Gln Phe Pro Gly Leu Thr Ile Ala Asn Glu
 50                  55                  60
Ala Glu Gly Gly Ala Thr Ala Val Ala Tyr Asn Lys Ile Ser Trp Asp
 65                  70                  75                  80
Pro Lys Tyr Gln Val Ile Asn Asn Leu Asp Tyr Glu Val Thr Gln Phe
                 85                  90                  95
Leu Gln Lys Asp Ser Phe Lys Pro Asp Asp Leu Val Ile Leu Trp Val
                100                 105                 110
```

```
Gly Ala Asn Asp Tyr Leu Ala Tyr Gly Trp Asn Thr Glu Gln Asp Ala
            115                 120                 125

Lys Arg Val Arg Asp Ala Ile Ser Asp Ala Ala Asn Arg Met Val Leu
130                 135                 140

Asn Gly Ala Lys Gln Ile Leu Leu Phe Asn Leu Pro Asp Leu Gly Gln
145                 150                 155                 160

Asn Pro Ser Ala Arg Ser Gln Lys Val Val Glu Ala Val Ser His Val
                165                 170                 175

Ser Ala Tyr His Asn Lys Leu Leu Asn Leu Ala Arg Gln Leu Ala
            180                 185                 190

Pro Thr Gly Met Val Lys Leu Phe Glu Ile Asp Lys Gln Phe Ala Glu
            195                 200                 205

Met Leu Arg Asp Pro Gln Asn Phe Gly Leu Ser Asp Val Glu Asn Pro
210                 215                 220

Cys Tyr Asp Gly Gly Tyr Val Trp Lys Pro Phe Ala Thr Arg Ser Val
225                 230                 235                 240

Ser Thr Asp Arg Gln Leu Ser Ala Phe Ser Pro Gln Glu Arg Leu Ala
                245                 250                 255

Ile Ala Gly Asn Pro Leu Leu Ala Gln Ala Val Ala Ser Pro Met Ala
            260                 265                 270

Arg Arg Ser Ala Ser Pro Leu Asn Cys Glu Gly Lys Met Phe Trp Asp
            275                 280                 285

Gln Val His Pro Thr Thr Val Val His Ala Ala Leu Ser Glu Arg Ala
            290                 295                 300

Ala Thr Phe Ile Glu Thr Gln Tyr Glu Phe Leu Ala His Gly
305                 310                 315

<210> SEQ ID NO 3
<211> LENGTH: 124
<212> TYPE: PRT
<213> ORGANISM: Aspergillus niger
<220> FEATURE:
<221> NAME/KEY: MISC_FEATURE
<223> OTHER INFORMATION: phospholipase A2 enzyme which acts on N-acyl
      phosphatidyl ethanolamine at the sn2 position found in MAXAPAL A2.

<400> SEQUENCE: 3

Ala Leu Trp Gln Phe Arg Ser Met Ile Lys Cys Ala Ile Pro Gly Ser
1               5                   10                  15

His Pro Leu Met Asp Phe Asn Asn Tyr Gly Cys Tyr Cys Gly Leu Gly
            20                  25                  30

Gly Ser Gly Thr Pro Val Asp Glu Leu Asp Arg Cys Cys Glu Thr His
        35                  40                  45

Asp Asn Cys Tyr Arg Asp Ala Lys Asn Leu Asp Ser Cys Lys Phe Leu
50                  55                  60

Val Asp Asn Pro Tyr Thr Glu Ser Tyr Ser Tyr Ser Cys Ser Asn Thr
65                  70                  75                  80

Glu Ile Thr Cys Asn Ser Lys Asn Asn Ala Cys Glu Ala Phe Ile Cys
                85                  90                  95

Asn Cys Asp Arg Asn Ala Ala Ile Cys Phe Ser Lys Ala Pro Tyr Asn
            100                 105                 110

Lys Glu His Lys Asn Leu Asp Thr Lys Lys Tyr Cys
            115                 120

<210> SEQ ID NO 4
<211> LENGTH: 167
```

```
<212> TYPE: PRT
<213> ORGANISM: Myceliophthora thermophila
<220> FEATURE:
<221> NAME/KEY: MISC_FEATURE
<223> OTHER INFORMATION: phospholipase A2 enzyme (CRC08335) which acts
      on NAPE (N-acyl phosphatidyl ethanolamine) at the sn2 position

<400> SEQUENCE: 4

Leu Pro Ser Ile Gly Lys Ala Asp Ala Ala Leu Val Pro Arg Gln Ser
1               5                   10                  15

Ala Ile Gln Ile Thr Asp Gln Tyr Leu Phe Asp Leu Thr Leu Pro Ala
            20                  25                  30

Phe Thr Ala Lys Arg Asn Ala Arg Asp Pro Pro Ser Leu Ile Trp Asp
        35                  40                  45

Ser Asp Gly Cys Ser Ser Pro Asp Asn Pro Phe Gly Phe Pro Phe
    50                  55                  60

Val Pro Ala Cys His Arg His Asp Phe Gly Tyr Arg Asn Tyr Lys Ala
65                  70                  75                  80

Gln Asn Arg Phe Thr Asp Ala Gly Lys Leu Ser Ile Asp Asn Asn Phe
                85                  90                  95

Lys Ser Asp Leu Tyr Tyr Gln Cys Glu Ser Val Ser Ala Lys Thr Ala
            100                 105                 110

Cys Arg Ala Leu Ala Asp Val Tyr Tyr Ala Ala Val Arg Ala Phe Gly
        115                 120                 125

Gly Ser Thr Gln Asp Lys Arg Asp Asp Leu Val Lys Ile Tyr Glu
    130                 135                 140

Glu Lys Val Ala Ile Tyr Asn Lys Ala Val Glu Glu Ala Gln Ala Lys
145                 150                 155                 160

Gly Glu Leu Trp Thr Leu Asp
                165

<210> SEQ ID NO 5
<211> LENGTH: 549
<212> TYPE: DNA
<213> ORGANISM: Myceliophthora thermophila
<220> FEATURE:
<221> NAME/KEY: misc_feature
<223> OTHER INFORMATION: synthetic gene encoding a fungal phospholipase
      A2 enzyme (CRC08335) which acts on NAPE (N-acyl phosphatidyl
      ethanolamine) at the sn2 position

<400> SEQUENCE: 5
atgaagttcc tgagcaccgc actttgcctt gcatcttctg tcctggcact tccatctatc    60
ggtaaagcag acgcagcact tgttccacgt caatctgcaa tccagatcac cgaccagtac   120
cttttcgacc ttacccttcc agcattcacc gcaaaacgta acgcacggga tccaccatct   180
cttatctggg attctgacgg ctgtagctct tctccagata acccattcgg cttcccattc   240
gttcctgctt gtcatcggca tgatttcggt taccggaact acaaggcaca gaaccgtttc   300
accgacgcag gcaagctttc tattgacaac aacttcaaga gcgacctcta ctaccagtgc   360
gagtctgttt ctgcaaagac agcttgtcgg gcacttgcag acgtctatta cgcagcagtt   420
cgggcattcg gaggttctac acaagataag cgggacgacg atctagttaa gatctacgaa   480
gagaaggtcg ccatctacaa caaggcagtt gaagaggcac aagcaaaggg cgagctttgg   540
acacttgat                                                            549

<210> SEQ ID NO 6
<211> LENGTH: 16
<212> TYPE: PRT
```

```
<213> ORGANISM: Myceliophthora thermophila
<220> FEATURE:
<221> NAME/KEY: MISC_FEATURE
<223> OTHER INFORMATION: N-terminal signal peptide sequence per
      prediction

<400> SEQUENCE: 6

Met Lys Phe Leu Ser Thr Ala Leu Cys Leu Ala Ser Ser Val Leu Ala
1               5                   10                  15
```